(12) United States Patent
Hochberg

(10) Patent No.: US 7,015,211 B2
(45) Date of Patent: Mar. 21, 2006

(54) 15α-SUBSTITUTED ESTRADIOL CARBOXYLIC ACID ESTERS AS LOCALLY ACTIVE ESTROGENS

(75) Inventor: Richard Hochberg, Guilford, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 10/796,462

(22) Filed: Mar. 9, 2004

(65) Prior Publication Data

US 2004/0198711 A1    Oct. 7, 2004

Related U.S. Application Data

(60) Provisional application No. 60/456,374, filed on Mar. 21, 2003.

(51) Int. Cl.
*A61K 31/565*  (2006.01)
*C07J 1/00*  (2006.01)

(52) U.S. Cl. ........................ 514/182; 552/629

(58) Field of Classification Search ............... 514/182; 552/629
See application file for complete search history.

(56) References Cited

OTHER PUBLICATIONS

Linder et al., "Preparation of Estrone and Estradiol Antigens through Carbon 15 of these Estrogens" Steroids, 1977, vol. 29(2), pp. 161-170.*
Linder et al. "Preparation of Estrone and Estradiol Antigens through Carbon 15 of these Estrogens" *Steroids*. Feb. 1977, vol. 29, No. 2, pp. 161-170.

* cited by examiner

*Primary Examiner*—Barbara P. Badio
(74) *Attorney, Agent, or Firm*—Henry D. Coleman; R. Neil Sudol; William J. Sapone

(57) ABSTRACT

The present invention relates to analogs of estradiol, which, in their most preferred embodiment, act as locally active estrogens without significant systemic action. A series of 15α-estradiol ester compounds is presented which exhibit excellent biological activity for use in pharmaceutical compositions for the treatment of symptomology associated with menopause. The present invention is therefore directed to compounds according to the structure:

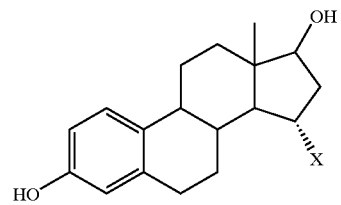

where X is

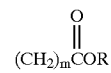

R is H, a $C_1$ to $C_5$ alkyl group, optionally substituted with at least one halogen group, such as $CH_2CH_2F$, or other group (e.g., $CH_2CHF_2$, $CH_2CF_3$ or $CF_3$ group); and
m is from 0–5, preferably from 0–2.

38 Claims, 4 Drawing Sheets

15α-SUBSTITUTED ESTRADIOL CARBOXYLIC ACID ESTERS AS LOCALLY ACTIVE ESTROGENS

RELATED APPLICATIONS

This application claims the benefit of priority from provisional application 60/456,374, filed Mar. 21, 2003, entitled 15α-Substituted Estradiol Carboxylic Acid Esters as Locally Active Estrogens.

FIELD OF THE INVENTION AND GRANT SUPPORT

The present invention relates to novel 15α-estradiol ester compounds and their use as locally active estrogens in the treatment of the symptomology of menopause. This invention was supported by NIH grant 5 R01 CA37799. The government retains certain rights in the invention.

BACKGROUND OF THE INVENTION

It is well recognized that pharmacologic estrogen administration (hormone replacement therapy, HRT) can alleviate most, if not all, of the symptomology associated with the menopause. These symptoms include, but are not limited to: bone loss associated with osteoporosis; heart disease associated with changes in blood lipids and lipoproteins; hot flashes; and vaginal dyspareunia.[1] However, there are risks associated with estrogen administration in HRT as well as oral contraceptive use, and include an association with endometrial cancer, breast cancer, and stroke. Although for the most part, the therapeutic benefits of HRT outweigh the risks, nevertheless, while the risks are small, they do exist.[2-4]

Estrogen therapy, directly and indirectly, affects a number of organs. Some of the outcomes associated with estrogen therapy are deleterious. Consequently, where possible, symptomology which could be ameliorated by local rather than systemic administration could limit the adverse side-effects of estrogen therapy. One such syndrome that can be treated directly, caused by estrogen deprivation or estrogen antagonists, is vaginal dyspareunia. It is a common disorder which affects a large proportion of women, approximately 40% within 10 years of the onset of the menopause.[5] It is an important factor in the quality of life for women so afflicted, as it is associated with a severe physical and psychological impact. It is not only painful but it can dramatically influence a women's self image and lead to clinical depression.[6] Another possible use of local estrogens includes topical administration to aging skin. The skin contains ER and it is an estrogen target organ.[7-9] While topical application of estrogens to the vaginal mucosa has been used to treat vaginal dyspareunia of the menopause, these estrogens are adsorbed into the blood and result in significant blood levels of estrogens.[10-13] Thus, this therapy may not be used where systemic estrogens are contraindicated.

Since topically applied estrogen is adsorbed into the blood, its purpose is defeated. A potent estrogen whose range is limited to the tissue to which it is applied would be ideal for the treatment of these disorders. Similar therapeutic agents with locally limited actions have been termed "soft drugs"[14], compounds which have a limited region of activity due to rapid metabolic inactivation. Ester groups have been used to convey "soft drug" properties to biologically active molecules because hydrolytic enzymes, including esterases, are ubiquitously distributed.[15] The ester containing compounds are the active agents while their hydrolysis products, the carboxylic acids, are inactive. In this manner, locally active glucocorticoids have been developed as antiinflammatory agents for the skin. These are esters of steroids substituted with a carboxylic acid group. The parent carboxylic acids do not bind to the glucocorticoid receptor and are biologically inert while their corresponding esters bind to the glucocorticoid receptor with high affinity.[16,17] The esters are rapidly hydrolyzed to the parent steroidal-carboxylic acid and thus, are inactivated by the ubiquitous esterases. Consequently, they can be used as anti-inflammatory agents for skin because their action is localized to the area to which they were applied, i.e., their rapid inactivation prevents systemic action.[18]

Similarly, in a study designed to produce affinity chromatographic supports for the purification of the estrogen receptor (ER) it was found that carboxylic acid analogs of estradiol ($E_2$) at C-7α- and C-17α are very poor ligands if they bind at all, but the methyl esters of these same analogs have much improved affinity for the ER.[19] It appears from those results that a charged carboxylic acid group in proximity to the steroid ring interferes with binding to the ER and that masking the charge by esterification reverses this interference.

In order to synthesize a locally active estrogen we previously described a series of compounds in which analogs of estradiol ($E_2$) were modified at 16α-with a series of carboxylic esters to produce a locally active estrogen that could be applied directly into and act solely within the vagina, without producing systemic effect.[20] Our design for a locally active estrogen is based upon the synthesis of analogs of estradiol containing carboxylates in proximity to the steroid nucleus. These organic acids have poor affinity for the estrogen receptor while esters of these same carboxylic acids bind very well to this receptor[20]. To be restricted to local action, these potent estrogens would be rapidly inactivated by esterases. The 16α-carboxylates of $E_2$ that we described were designed and tested for the following characteristics: affinity for the estrogen receptor; biological activity in an in vitro estrogen sensitive model (endometrial cells in culture); as substrates for esterase hydrolysis; local action through in vivo estrogenic stimulation of the vagina; systemic activity (uterotrophic action). Two of these $E_2$-analogs, the ethyl and 2'-monofluorethyl esters of $E_2$-16α-formate showed the requisite properties with significant differences in their systemic and local actions. Our aim in the present study was to design a second generation of local estrogens with increased estrogenic potency leading to greater local action and yet decreased systemic action. To this end we synthesized carboxylic esters of estradiol at 15α, at which substituents are known to be tolerated by the estrogen receptor.[21] These esters and carboxylic acids were tested for estrogenic potential (binding to the estrogen receptor; in vitro bioassay; in vivo, vaginal and uterotrophic assays) and as substrates for esterase enzyme(s).

OBJECTS OF THE INVENTION

It is an object of the invention to provide novel compounds and pharmaceutical compositions for use in treating the symptomology of menopause.

It is an additional object of the invention to provide a form of estrogen which may be used to provide a therapeutic effect while limiting deleterious effects which may occur with systemic administration of estrogenic steroids.

It is yet another object of the invention to provide methods for treating the symptomology of menopause, especially including vaginal dyspareunia.

It is still another object of the invention to provide topical dosage forms of the present compounds, and in particular, vaginal creams, gels and lotions for use in the treatment of certain symptoms associated with menopause, especially vaginal dyspareunia.

These and/or other objects of the invention may be readily gleaned from a review of the description of the invention which follows.

SUMMARY OF THE INVENTION

Figure 1:
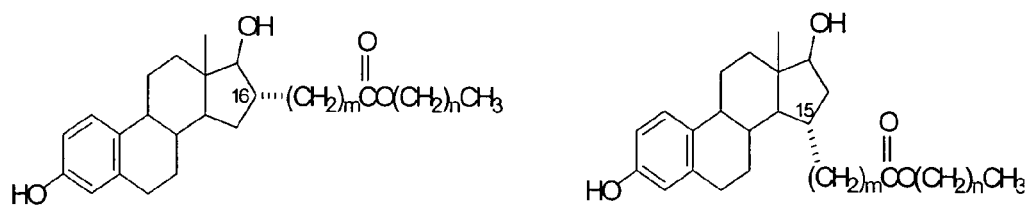
FIG. 1 illustrates novel 15α-estradiol ester compounds of the invention. Abbreviation key for the $E_2$-carboxy esters: Ex-(m+1), (n+1): where x is the position in the steroid nucleus from which the ester chain originates and the quantity (m+1) is the number of carbon atoms in the acid and (n+1), the alcohol portion of the chain containing the ester.

The present invention is directed to compounds according to the structure:

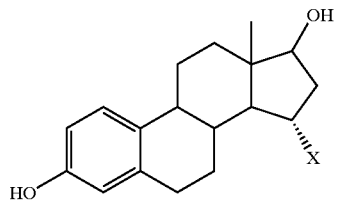

where X is

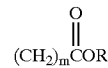

R is H, a $C_1$ to $C_5$ alkyl group, optionally substituted with at least one halogen group, preferably no more than three halogen groups, more preferably at least one F group, such as a $CH_2CH_2F$ or other group, (e.g., $CH_2CHF_2$, $CH_2CF_3$ or $CF_3$ group);

m is from 0–5, preferably from 0–2 and pharmaceutically acceptable salts, solvates and polymorphs, thereof.

Preferred compounds according to the present invention may be depicted according to the structural formula where substitutent X is disposed in an alpha configuration (i.e., disposed or oriented below the planar surface of the molecule).

The present invention also relates to pharmaceutical compositions according to the present invention comprising an effective amount of at least one compound as described above in combination with a pharmaceutically acceptable carrier, additive or excipient. Preferably, pharmaceutical compositions according to the present invention are formulated in topical dosage form, more preferably as vaginal creams, gels or suppositories for local delivery of the active compounds to the patient.

In another aspect of the present invention, a therapeutic treatment comprises administering one or more of the active compounds according to the present invention to a patient in need of therapy for the treatment of the symptomology associated with menopause. Preferred aspects of the present invention include the treatment of vaginal dyspareunia in patients in need of such therapy, especially in patients for which systemic estrogens are contraindicated, comprising topically administering to the vaginal area of such a patient an effective amount of one or more active compound according to the present invention in pharmaceutical dosage form (preferably, as a vaginal gel, cream, lotion or suppository).

Compounds according to the present invention may also be used as synthetic intermediates to produce pharmaceutically active compounds according to the present invention or related compounds.

DETAILED DESCRIPTION OF THE INVENTION

The following terms shall be used throughout the specification to describe the present invention.

The term "patient" is used throughout the specification to describe an animal, preferably a human, to whom treatment, including prophylactic treatment, with the compounds according to the present invention is provided. For treatment of the symptomology, conditions or disease states which are specific for a specific animal such as a human patient, the term patient refers to that specific animal. In most instances in the present invention, the patient is a human female exhibiting symptomology associated with menopause.

The term "effective amount" is used throughout the specification to describe concentrations or amounts of compounds according to the present invention which may be used in context to produce a favorable change in the symptomology, disease or condition treated, whether that change is a decrease in or reversal of the effects of symptomology or disease state depending upon the disease state or condition treated. In the present invention, in preferred aspects, an effective amount is that amount which is used to treat the symptomology associated with menopause, in its most preferred aspect, vaginal dyspareunia. An effective amount for purposes of treating one or more disease states or symptoms of the present invention, includes the timing and manner in which an active compound is administered to a patient.

The term "alkyl" is used throughout the specification to describe a hydrocarbon radical containing between one and five carbon units. Alkyl groups for use in the present invention include linear or branched-chain groups such as methyl, ethyl, propyl, i-propyl, butyl, sec-butyl, tert-butyl, pentyl, neo-pentyl, etc.

The term "menopause" is used throughout the specification to describe the period in a woman's life between the ages of approximately 45 and 50 after which menstruation (menses) naturally ceases. The symptomology associated with menopause which is particularly relevant to the present invention includes bone loss associated with osteoporosis and most importantly, vaginal dyspareunia.

The term "vaginal dyspareunia" is used throughout the specification to describe a symptom or condition of menopause wherein vaginal atrophy, dryness and pain during sexual intercourse occurs.

A preferred therapeutic aspect according to the present invention relates to methods for treating the symptomology of menopause comprising administering therapeutically effective amounts or concentrations of one or more of the compounds according to the present invention to treat the symptomology associated with menopause in the patient. This symptomology preferably includes bone loss associated with osteoporosis and vaginal dyspareunia. In each of these cases, local delivery of compounds according to the present invention may take maximum advantage of the local effects of the compounds in vivo.

Pharmaceutical compositions based upon these novel chemical compounds comprise the above-described compounds in a therapeutically effective amount for the treatment of the symptomology of menopause or a related condition or disease state, optionally in combination with a pharmaceutically acceptable additive, carrier or excipient. Pharmaceutical compositions in topical dosage form, preferably for local delivery of the active compounds, especially vaginal creams, gels and lotions, are particularly preferred.

Certain of the compounds, in pharmaceutical dosage form, may be used as prophylactic agents for preventing or reducing the likelihood of a patient exhibiting specific symptomology associated with menopause.

Modifications of the active compound can affect the solubility, bioavailability and rate of metabolism of the active species, thus providing control over the delivery of the active species. Further, the modifications may affect the activity of the compound, in some cases increasing the activity over the parent compound. This can easily be assessed by preparing the derivative and testing its activity according to known methods well within the routineer's skill in the art.

The compounds of this invention may be incorporated into formulations for all routes of administration including without limitation transdermal and in suppository form. Topical dosage forms include skin delivery vehicles as well as, more preferably, creams, lotions, gels and suppositories which can be delivered to the vaginal membranes.

Pharmaceutical compositions based upon these novel chemical compounds comprise the above-described compounds in a therapeutically effective amount for treating the symptomology of menopause which have been described hereinabove, especially including vaginal dyspareunia, optionally in combination with a pharmaceutically acceptable additive, carrier and/or excipient. One of ordinary skill in the art will recognize that a therapeutically effective amount of one of more compounds according to the present invention will vary with the condition or symptomology to be treated, its severity, the treatment regimen to be employed, the pharmacokinetics of the agent used, as well as the patient to be treated.

In the pharmaceutical aspect according to the present invention, the compound according to the present invention is formulated preferably in admixture with a pharmaceutically acceptable carrier. In general, it is preferable to administer the pharmaceutical composition in topically administrable form, especially including vaginal creams, gels, lotions and suppositories, but a number of formulations may be administered via other route. Of course, one of ordinary skill in the art may modify the formulations within the teachings of the specification to provide numerous formulations for a particular route of administration, if desired, without rendering the compositions of the present invention unstable or compromising their therapeutic activity, noting that the ester groups (R) are somewhat labile. In particular, the modification of the present compounds to render them more soluble in water or other vehicle, for example, may be accomplished by minor modifications which are well within the ordinary skill in the art. It is also well within the routineer's skill to modify the route of administration and dosage regimen of a particular compound in order to manage the pharmacokinetics of the present compounds for maximum beneficial effect to the patient.

The amount of compound included within therapeutically active formulations according to the present invention is an effective amount for treating the symptom or condition. In its most preferred embodiments, the present compounds are administered topically to vaginal membranes for treating the symptomology of vaginal dyspareunia. In general, a therapeutically effective amount of the presently preferred compound in dosage form usually ranges from slightly less than about 0.001 mg./kg. to about 1.0 g./kg., preferably about 0.01 mg/kg to about 0.1 mg/kg of the patient or considerably more depending upon the compound used, the condition or symptomology treated and the route of administration, although exceptions to this dosage range may be contemplated by the present invention and are well within the teachings of the present invention.

Administration of the active compound preferably occurs via a topical dosage route, and preferably via a vaginal cream, gel, lotion or vaginal suppository. In certain aspects, administration may include other routes of administration such as transdermal (including an optional penetration enhancer), among other routes. Other routes of administration may include, for example, local delivery at the site of administration, for example, from an implanted material (such as an artificial hip or other prosthesis), among others. Preferably, the active compounds are administered via a topical route, most preferably as vaginal creams, gels, lotions or suppositories for administration to the vaginal membranes or vaginal cavity of the patient.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., topical or other route as appropriate. In preparing pharmaceutical compositions in the preferred topical dosage form, any of the usual pharmaceutical media may be used including thickeners, emollients, emulsifiers, etc. may be used to produce creams, gels, salves, ointments and the like for topical delivery, most preferably to the vaginal membranes. Administration via a vaginal suppository is also preferably contemplated by the present invention.

In the case of oral dosage forms, liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques.

For parenteral formulations, the carrier will usually comprise sterile water or aqueous sodium chloride solution, though other ingredients including those which aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

The present compounds may be used to treat animals, and in particular, mammals, especially including humans, especially females as patients. Patients may be treated by administering to the patient an effective amount of one or more of the compounds according to the present invention optionally in a pharmaceutically acceptable carrier or diluent, either alone, or in combination with other known pharmaceutical agents, depending upon the condition or symptomology to be treated. This treatment can also be administered in conjunction with other conventional menopausal therapies.

The active compound is included in the pharmaceutically acceptable carrier or diluent in an amount sufficient to deliver to a patient a therapeutically effective amount for the desired indication, without causing toxic effects in the patient treated.

The compound is conveniently administered in any suitable unit dosage form, including but not limited to one containing less than 1 mg (preferably, at least 1 mg) to 3000 mg, preferably 5 to 500 mg of active ingredient per unit dosage form. A topical dose ranging from about 5 to about 250 mg is usually convenient.

The concentration of active compound in the drug composition will depend on absorption, distribution, inactivation, and excretion rates of the drug as well as other factors known to those of skill in the art. It is to be noted that dosage values will also vary with the severity of the condition or symptomology to be treated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time. In its most preferred aspect of the present invention, i.e., in the topical administration of compounds according to the present invention to the vaginal membranes of the patient to be treated, the active may be administered as infrequently as once every several days to several times a day, depending upon the activity of the compounds and other factors well known in the art.

Oral compositions, if used, will generally include an inert diluent or an edible carrier. They may be enclosed in gelatin capsules (soft or hard) or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The active compound may also be administered as a component of an elixir, suspension, syrup, wafer, chewing gum or the like. A syrup may contain, in addition to the active compounds, sucrose and/or corn syrup as a sweetening agent and certain preservatives, dyes and colorings and flavors.

The active compound can also be mixed with other active materials which do not impair the desired action, or with materials which supplement the desired action, such as other hormonal agents, and in other instances depending upon the desired therapy or target, other pharmaceutically active compounds.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. If administered intravenously, preferred carriers include, for example, physiological saline or phosphate buffered saline (PBS). In the case of the preferred pharmaceutical compositions in topical dosage forms for delivery to vaginal membranes, creams, gels and/or viscous lotions may be used as vaginal delivery forms. Creams, gels, lotions and suppositories may be formulated using standing pharmaceutical procedures.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid, among others. Methods for preparation of such formulations are well known and will be readily apparent to those skilled in the art.

Liposomal suspensions may also be pharmaceutically acceptable carriers. These may be prepared according to methods known to those skilled in the art. For example, liposome formulations may be prepared by dissolving appropriate lipid(s) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension. Other methods of preparation well known by those of ordinary skill may also be used in this aspect of the present invention.

The present invention relates to a family of carboxylic acid esters of estradiol at the 15α-position in the steroid nucleus at which bulky substituents are accommodated by the estrogen receptor. These compounds were tested for estrogen receptor binding (estrogen receptors α and β); stimulation of an estrogen sensitive gene in Ishikawa cells in culture; and as substrates for enzymatic hydrolysis. Likely candidates were tested in in vivo assays for systemic and local estrogenic action. The biological studies showed that regardless of the point of attachment, all of the short chain carboxylic acids, C-1 to C-3, were devoid of hormonal action, while many of the esters were estrogenic. Formate esters at 15α- were good estrogens, but lengthening the chain to acetate dramatically decreased hormonal activity. In general, the length of the alcohol from methyl to butyl had only small effect on receptor binding, and as the size of the alcohol increased, so did esterase hydrolysis. Several of the esters were tested in vivo and two, the methyl and ethyl esters of estradiol-15α-formate, appeared to have the requisite properties (high local and low systemic activity) of superior "soft" estrogens.

SYNTHETIC CHEMISTRY

The following describes the general chemical steps which were carried out to provide the compounds according to the present invention. The general synthetic schemes are presented in FIGS. 2, 3, and 4.

Figure 2:
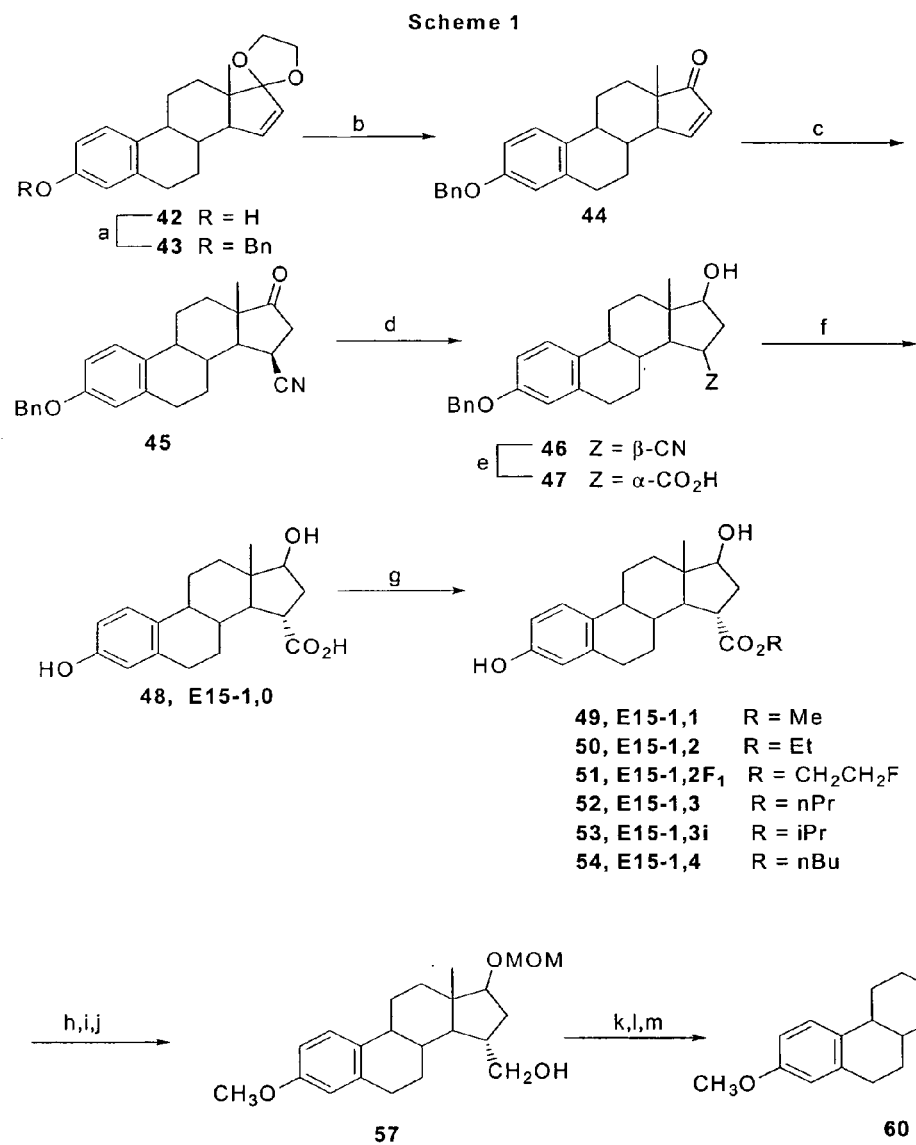
FIG. 2, Scheme 1 shows the chemical synthesis of 15α-formyl ester analogs and individual chemical steps and reagents used to effect those steps: (a) BnBr, $K_2CO_3$, $iPr_2NEt$, acetone (42→43); (b) pTsOH, acetone (43→44); (c) NaCN, THF, 75° C. (44→45); (d) $NaBH_4$, MeOH, THF (45→46); (e) KOH, ethylene glycol 160° C. (46→47); (f) 5% Pd—C/$H_2$, EtOH (47→48); (g) ROH, $H_2SO_4$ (48→49–54); (h) $CH_3I$, $K_2CO_3$, acetone 60° C. (50→55); (i) MOMCl, $iPrEt_2N$, toluene (55→56); (O) $LiAlH_4$, $Et_2O$ (56→57); (k) pTsCl, pyridine, 4° C. (57→58); (l) $LiEt_3BH$, THF, 65° C. (58→59); (m) HCl-MeOH (59→60).

The synthesis of the 15α-formyl ester analogues of estradiol 49–54 is shown in FIG. 2, Scheme 1 and employs methodology used previously by Bernstein to prepare 15α-carboxyl substituted estradiol derivatives.[22,23] Ketal 42[24] was protected as the 3-benzyl ether 43 and carefully deketalized with pTsOH in aqueous acetone at rt to give enone 44. Conjugate addition of NaCN in aqueous THF at reflux gave the 15β-cyano steroid 45. Ketone reduction followed by nitrile hydrolysis gave the 15α-carboxylic acid 47 via epimerization of the intermediate carboxamide. Hydrogenolysis of 47 with 5% Pd—C/H$_2$ gave the acid 48, E15-1,0. The methyl, ethyl, trifluoroethyl, n-propyl, isopropyl and n-butyl esters [E15-1,1 (49), E15-1,2 (50), E15-1,2 F$_1$ (51), E15-1,3 (52), E15-1,3i (53) and E15-1,4 (54)] were prepared by reacting 48 with the appropriate alcohol in the presence of a catalytic amount of H$_2$SO$_4$.

To support the assignment of stereochemistry at C-15, the ester function of E15-1,2 (50) was converted to a methyl group giving the known 3-methoxy-15α-methyl-1,3,5(10)-estratriene-17β-ol 60[25] as follows (FIG. 2, Scheme 1). Methylation of the phenolic hydroxyl group followed by protection of the 17β-hydroxyl group as the MOM-ether gave 56. Reduction of the 15-ester with LiAlH$_4$, a reagent known not to affect epimerizable asymmetric centers[26,27] gave the hydroxymethyl steroid 57 which was tosylated giving 58. Reductive removal of the tosyl group followed by deprotection of the 17-hydroxyl group yielded 60 whose $^1$H NMR was identical with that reported in the literature.[25] In addition there is a triplet signal (J=10.2 Hz) for H-14α at δ 0.90 ppm in the $^1$H NMR spectrum of 60, indicating a trans-diaxial relationship with both H-8 and H-15, and is in accord with that seen with other 15α-substituted estradiol compounds.[28]

Figure 3:
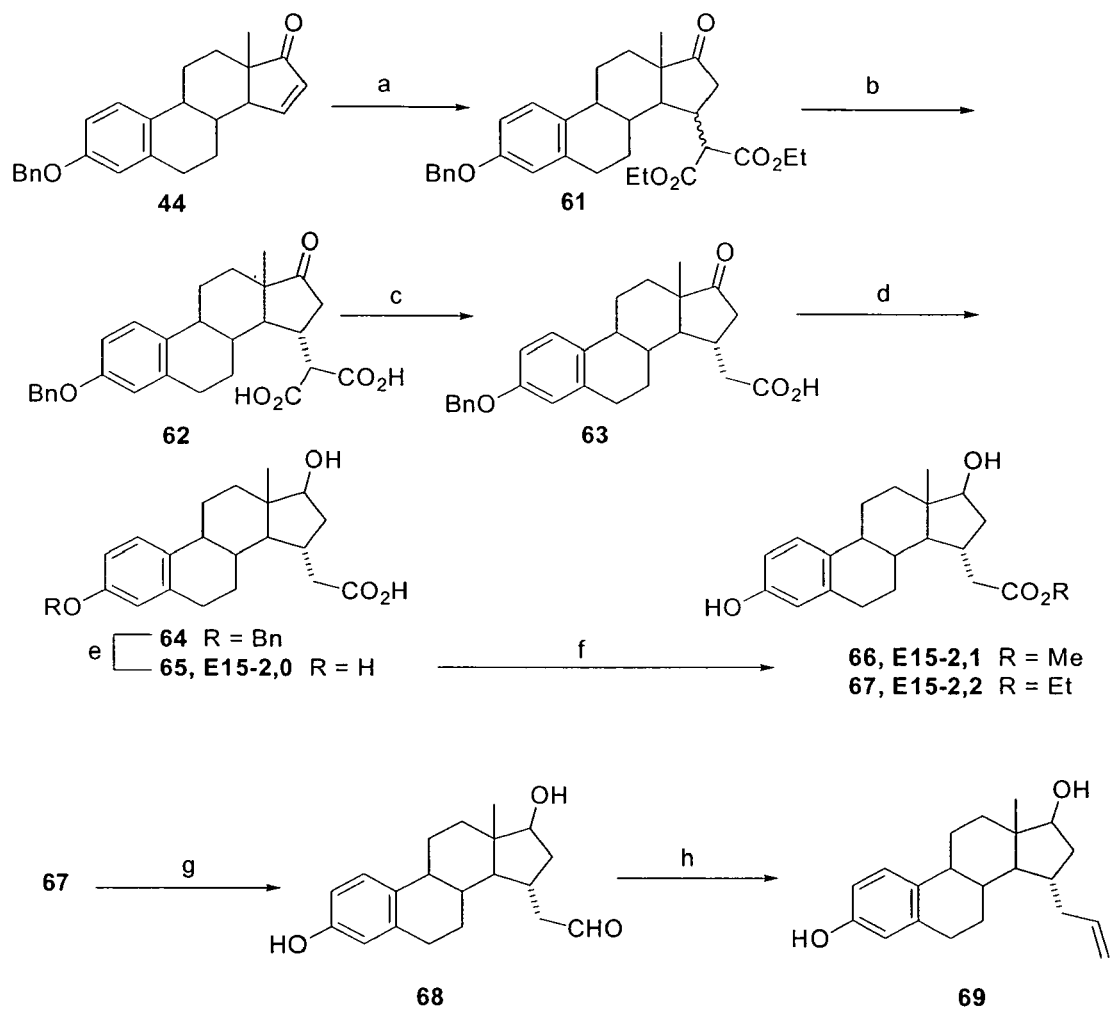
FIG. 3, Scheme 2 shows the chemical synthesis of 15α-carboxymethyl analogs of estradiol and individual chemical steps and reagents used to effect those steps: (a) i) NaH, diethyl malonate, THF ii) 44 (44→61α,β); (b) NaOH, EtOH, $H_2O$ (61→62); (c) diglyme, 162° C. (62→63); (d) $NaBH_4$, EtOH (63→64); (e) 5% Pd—C/$H_2$, EtOH (64→65); (f) $SOCl_2$, ROH, 40° C. (65→66,67); (g) DIBAL, toluene, −60° C. (67→68); (h) Nystead reagent, $BF_3.OEt_2$, THF (68→69).

The synthesis of the 15α-carboxymethyl analogues of estradiol 65–67 is shown in FIG. 3, Scheme 2 and uses the procedure employed by Kojima to prepare 15α-carboxymethyltestosterone derivatives.[29] Sodium diethylmalonate was added to enone 44 in a Michael reaction to give mainly the α-epimer of 61. Ester hydrolysis followed by decarboxylation produced only the 15α-carboxymethyl steroid 63. Ketone reduction with NaBH$_4$ followed by deprotection with 5% Pd—C/H$_2$ gave the acid E15-2,0, 65. The esters E15-2,1 66 and E15-2,2 67 were prepared by reacting 65 with the appropriate alcohol in the presence of SOCl$_2$. Confirmation of the stereochemistry at C-15 was provided by conversion of 67 to the known 15α-allylestradiol 69[30] (FIG. 3, Scheme 2) by DIBAL reduction to 68 followed by methyleneation with Nystead reagent to 69. The $^1$H NMR spectrum of 69 is identical to that reported for 15α-allylestradiol. In particular the signal for H-14α of 15α-allylestradiol 69 appears as a distinct triplet at δ 1.00 ppm with J=10.0 Hz, whereas the signal for H-14α of the β-allyl epimer would be contained in a region of overlapping signals δ 1.1–1.5 ppm.[30] In addition, this triplet signal at δ 1.00 ppm is present in the $^1$H NMR spectrum of each of the 15α-carboxymethyl steroids 65–67.

Figure 4:
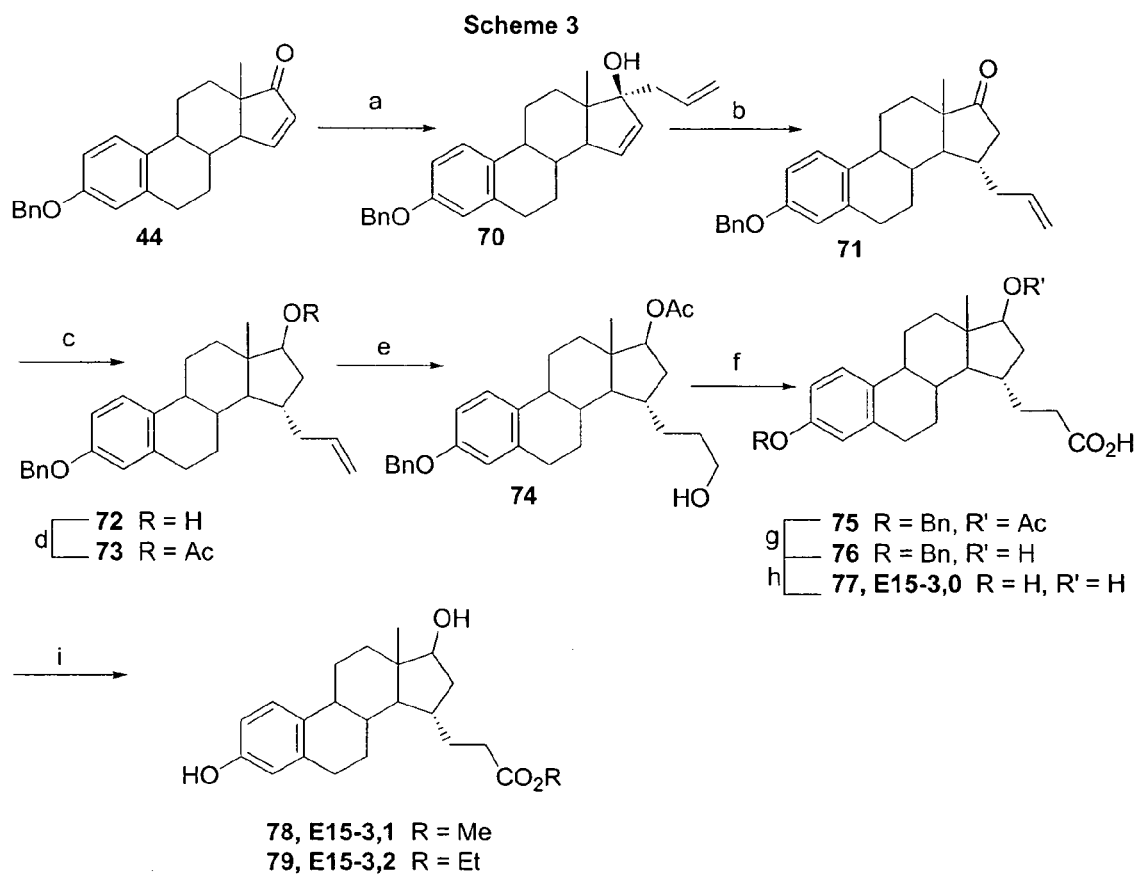
FIG. 4, Scheme 3 shows the chemical synthesis of 15α-carboxyethyl analogs of estradiol and individual chemical steps and reagents used to effect those steps: (a) allylmagnesium chloride, THF, 0° C. (44→70); (b) KH, THF, 18-crown-6 (70→71); (c) $NaBH_4$ THF (71→72); (d) $Ac_2O$, pyridine (72→73); (e) i) $BH_3$.THF, THF ii) $Me_3NO$, 150° C. (73→74); (f) $CrO_3$—$H_2SO_4$, acetone, 0° C. (74→75); (g) KOH, MeOH, 55° C. (75→76); (h) 5% Pd—C/$H_2$, EtOH (76→77); (i) $SOCl_2$, ROH (77→78,79).

The synthesis of the 15α-carboxyethyl analogues of estradiol 77–79 is shown in FIG. 4, Scheme 3 and is based on methodology used previously by Bojack et al[28] and Dionne et al[30] to prepare 15α-allylestradiol. The 1,2-addition of allylmagnesium chloride to enone 44 in THF at 0° C. gave 70 as the only isomer. Anionic oxy-Cope rearrangement with KH and 18-crown-6 in THF produced exclusively the 15α-allylestrone 71. Reduction of the 17-ketone followed by acetylation of the resulting 17β-alcohol gave 73. Hydroboration of 73 followed by oxidation with trimethylamine N-oxide in diglyme produced the alcohol 74, which was oxidized with CrO$_3$—H$_2$SO$_4$ to give the acid 75. Saponification of the acetate group followed by hydrogenolysis of the benzyl group gave E15-3,0 77. Esterification of 77 with the appropriate alcohol and SOCl$_2$ gave E15-3,1 78 and E15-3,2 79.

The following non-limiting examples are provided to exemplify the present invention. One of ordinary skill will recognize that the presentation of these examples for purposes of exemplary teachings of the present invention and is not be construed as limiting the breadth of the invention in any way.

EXAMPLES

Materials and Methods. $^1$H NMR spectra were recorded with a Bruker AM500 and chemical shifts are reported relative to residual CHCl$_3$ (7.27 ppm) or DMSO (2.5 ppm). Purification by flash-chromatography was performed according to the procedure of[31] using 230–400 mesh silica gel (EM Science, Darmstadt Germany). High resolution mass spectra were obtained by electrospray ionization on a Micromass Q-Tof spectrometer by DR. Walter J. McMurray at the Yale University Comprehensive Cancer Center using either PEG as an internal standard with NH$_4$OAc or NaI as an internal standard. Elemental analyses were performed by Schwarzkopf Micro Analytical Laboratory, Woodside N.Y. The computer program Prism was purchased from GraphPad Software Inc. (San Diego, Calif.). The cell culture reagents were obtained from Gibco-BRL (Grand Island, N.H.). Unless otherwise indicated, solvents (analytical or HPLC grade) and reagents were used as supplied, and all reactions were carried out under nitrogen.

Chromatographic Systems. Thin-layer chromatography (TLC) was performed using Merck silica gel plates (F$_{254}$) (EM Science) and visualized using phosphomolybdic acid or UV illumination. TLC systems: T-1, hexanes/EtOAc (2:1); T-2, hexanes/EtOAc (1:1); T-3, CHCl$_3$/MeOH (5:1); T-4, hexanes/EtOAc (4:1). Analytical high-performance liquid chromatography (HPLC) was performed on a Waters 600E system (Waters Co. Milford Mass.) equipped with a 484 variable wavelength detector set at 280 nm using the following columns and systems. Ultrasphere ODS column (5 µm, 10 mm×25 cm, Altex Scientific Operations Co.) with the following solvent systems at 3 mL/min: H-1, HOAc/CH$_3$CN/H$_2$O (0.15:25:74.85); H-2, CH$_3$OH/H$_2$O (60:40); H-3, CH$_3$CN/H$_2$O (40:60); H-4, HOAc/CH$_3$CN/H$_2$O (0.13:35:64.87); H-5, CH$_3$CN/H$_2$O (50:50); H-6, HOAc/CH$_3$CN/H$_2$O (0.14:30:69.86); H-7, HOAc/CH$_3$CN/H$_2$O (0.12:40:59.88); H-8, CH$_3$CN/H$_2$O (45:55). LiChrospher 100 Diol column (5 µm, 4.6 mm×25 cm, EM Science) with the following solvent systems at 1 mL/min: H-9, CH$_2$Cl$_2$/iPrOH (90:10); H-10, CH$_2$Cl$_2$/iPrOH (99:1); H-11, CH$_2$Cl$_2$/iPrOH (98:2); H-12, CH$_2$Cl$_2$/iPrOH (95:5); H-13, HOAc/CH$_2$Cl$_2$/iPrOH (0.094:94.25:5.65); H-14, HOAc/CH$_2$Cl$_2$/iPrOH (0.1:6:93.9); H-15, CH$_2$Cl$_2$; H-16, CH$_2$Cl$_2$/isooctane (80:20); H-17, HOAc/CH$_2$Cl$_2$/iPrOH (0.1:3:96.9); H-18, CH$_2$Cl$_2$/isooctane (90:10). Protein I-60 column (7.8 mm×30 cm, Waters Co.) with the following solvent systems at 3 mL/min: H-19, HOAc/iPrOH/CH$_2$Cl$_2$ (0.1:6:93.9); H-20, HOAc/iPrOH/CH$_2$Cl$_2$ (0.1:5.99:93.91); H-21, CH$_2$Cl$_2$; H-22, HOAc/iPrOH/CH$_2$Cl$_2$ (0.1:3:96.9). Beckman System Gold HPLC system (Beckman Coulter, Inc. Fullerton, Calif.) consisting of a model 126 solvent module and a model 168 diode array detector set at 280 nm using a Microsorb-MV C18 column (5 µm, 4.6 mm×25 cm, Varian Analytical Instruments) in the following solvent systems at 1 mL/min: H-23, HOAc/CH$_3$CN/H$_2$O (0.15:25:74.85); H-24, CH$_3$CN/H$_2$O (35:65); H-25, CH$_3$CN/H$_2$O (40:60); H-26, CH$_3$CN/H$_2$O (50:50); H-27, HOAc/CH$_3$CN/H$_2$O (0.13:35:64.87); H-28, CH$_3$CN/H$_2$O (45:55); H-29, HOAc/CH$_3$CN/H$_2$O (0.14:30:69.86); H-30, HOAc/CH$_3$CN/H$_2$O (0.13:33:66.87).

CHEMICAL SYNTHESIS OF COMPOUNDS

3-Benzyloxy-17,17-ethylenedioxyestra-1,3,5(10),15-tetraene (43). A solution of 1.90 g (6.07 mmol) of 42,[24] 940 µL (7.89 mmol) of benzylbromide, 1.09 (7.89 mmol) of K$_2$CO$_3$ and 1.06 mL (6.07 mmol) of diisopropylethylamine in 50 mL acetone was stirred at rt for 3 days. The reaction mixture was poured into H$_2$O (150 mL) and extracted with EtOAc (3×, 100 mL) Combined organic extracts were dried over Na$_2$SO$_4$ and concentrated in vacuo giving a yellow oil. Purification by flash chromatography on a 3×21 cm column of silica gel using 3:1 hexanes/EtOAc as eluent gave 2.37 g (97%) of 43. Data for 43: TLC, T-1, R$_f$ 0.54.

3-Benzyloxyestra-1,3,5(10),15-tetraen-17-one (44). A solution of 1.04 g (2.57 mmol) of 43, 117 mg (0.617 mmol) of pTsOH in acetone (70.3 mL) and H$_2$O (11.4 mL) was stirred at rt for 1.5 h. The reaction mixture was adjusted to pH 7 with 5% NaHCO$_3$ and concentrated by rotovap to about 30 mL without heating. The solution was poured into H$_2$O (50 mL) and extracted with EtOAc (3×, 70 mL). Combined organic extracts were dried over Na$_2$SO$_4$ and concentrated in vacuo giving a white solid. Crystallization of the residue from CH$_2$Cl$_2$/hexanes gave 477 g (52%) of 44 as fine white needles. Data for 44: TLC, T-1, R$_f$ 0.5; $^1$H NMR (400 MHz, CDCl$_3$) δ 1.12 (s, 3H, H-18), 5.05 (s, 2H, benzylic-H), 6.10 (dd, 1H, J=5.9, 3.2 Hz, H-15), 6.76 (d, 1H, J=2.7 Hz, H-4), 6.81 (dd, 1H, J=8.6, 2.7 Hz, H-2), 7.22 (d, 1H, J=8.6 Hz, H-1), 7.31–7.45 (m, 5H, Ar—H), 7.64 (dd, 1H, J=5.9, 1.1 Hz, H-16).

3-Benzyloxy-15β-cyanoestra-1,3,5(10)-trien-17-one (45). This procedure is based on the literature method.[22,23] A solution of 1.03 g (2.88 mmol) of 44, 2.03 g (41.5 mmol) of NaCN in THF (30 mL) with 21 drops of H$_2$O was stirred and heated at 75° C. under reflux for 2 h. The reaction mixture was poured into ice water (300 mL) and extracted with CH$_2$Cl$_2$ (3×, 100 mL). Combined organic extracts were washed with H$_2$O (100 mL), dried over Na$_2$SO$_4$ and concentrated in vacuo giving a brown oil. Purification by flash chromatography on a 3×17 cm column of silica gel using 2:1 hexanes/EtOAc as eluent gave 557 mg (50%) of 45 as a white solid. Data for 45: TLC, T-1, R$_f$ 0.3; $^1$H NMR (400 MHz, CDCl$_3$) δ 1.24 (s, 3H, H-18), 5.06 (s, 2H, benzylic-H), 6.76 (d, 1H, J=2.7 Hz, H-4), 6.81 (dd, 1H, J=8.6, 2.7 Hz, H-2), 7.20 (d, 1H, J=8.6 Hz, H-1), 7.33–7.45 (m, 5H, Ar—H).

3-Benzyloxy-15β-cyanoestra-1,3,5(10)-trien-17β-ol (46). A solution of 558 mg (1.45 mmol) of 45 in THF (6.6 mL) and MeOH (34 mL) was stirred at rt as 400 mg (10.6 mmol) of NaBH$_4$ was added in small portions over 10 min. The reaction was stirred at rt under N$_2$ for 3.5 h, the solvent was evaporated and the residue was dissolved in EtOAc (100 mL) and H$_2$O (50 mL). The phases were separated and the aqueous phase was extracted with EtOAc (2×, 70 mL). Combined organic extracts were dried over Na$_2$SO$_4$ and concentrated in vacuo giving a yellow foam which was used without purification in the next step. Data for 46: TLC, T-2, R$_f$ 0.22; $^1$H NMR (400 MHz, CDCl$_3$) δ 1.07 (s, 3H, H-18), 3.75 (t, 1H, J=8.7 Hz, H-17α), 5.05 (s, 2H, benzylic-H), 6.75 (d, 1H, J=2.7 Hz, H-4), 6.80 (dd, 1H, J=8.5, 2.7 Hz, H-4), 7.21 (d, 1H, J=8.5 Hz, H-1), 7.33–7.45 (m, 5H, Ar—H).

3-Benzyloxy-17β-hydroxyestra-1,3,5(10)-trien-15α-carboxylic acid (47). A solution of 571 mg (1.47 mmol) of 46 crude, 2.54 g (45.3 mmol) KOH in H$_2$O (6 mL) and ethylene glycol (34 mL) was stirred and heated at 160° C. for 112 h without a reflux condenser to allow H$_2$O to evaporate. The reaction mixture was poured into H$_2$O (700 mL) and washed with Et$_2$O (2×, 100 mL). The aqueous phase was adjusted to pH 2 with concentrated HCl and extracted with Et$_2$O (3×, 100 mL). Combined organic extracts were washed with 10% sodium metabisulfite (50 mL), H$_2$O (50 mL), dried over Na$_2$SO$_4$ and concentrated in vacuo giving 535 mg (89%, two steps) of 47 as a tan solid. Data for 47: TLC, T-3, R$_f$ 0.575; $^1$H NMR (400 MHz, DMSO-d$_6$) δ0.69 (s, 3H, H-18), 3.61 (ddd, 1H, J=8.7, 8.7, 5.0 Hz, H-17α), 4.73 (d, 1H, J=5.0 Hz, 17-OH), 5.04 (s, 2H, benzylic-H), 6.67 (d, 1H, J=2.6 Hz, H-4), 6.74 (dd, 1H, J=8.7, 2.6 Hz, H-2), 7.17 (d, 1H, J=8.7 Hz, H-1), 7.31–7.42 (m, 5H, Ar—H), 12.07 (s, 1H, OH).

3,17β-Dihydroxyestra-1,3,5(10)-trien-15α-carboxylic acid (48, E15-1,0). A solution of 479 mg (1.18 mmol) of 47 in EtOH (10 mL) was warmed to dissolve solid, cooled to rt, and added to a suspension of 50 mg 5% Pd on carbon in EtOH (5 mL) and stirred at rt under an atm of H$_2$ for 20 h. The reaction mixture was filtered through a 1" plug of Celite and washed through with EtOH (50 mL). The solvent was evaporated giving 368 mg (99%) of 48 as a white solid. Purification of 25.5 mg of this material by HPLC in system H-20 followed by acid/base extraction gave 11.9 mg 48 for bioassay. Data for 48: TLC, T-3, R$_f$ 0.475; $^1$H NMR (400 MHz, DMSO-d6) δ 0.69 (s, 3H, H-18), 3.60 (ddd, 1H, J=8.7, 8.7, 5.0 Hz, H-17α), 4.72 (d, 1H, J=5.0 Hz, OH), 6.40 (d, 1H, J=2.3 Hz, H-4), 6.49 (dd, 1H, J=8.5, 2.3 Hz, H-2), 7.04 (d, 1H, J=8.5 Hz, H-1), 9.00 (s, 1H, OH), 12.05 (br s, 1H, OH); HRMS (ES$^-$) calcd for C$_{19}$H$_{23}$O$_4$ (M–H) m/e 315.1597, found m/e 315.1603; HPLC system H-14, t$_R$=12.85 min, and system H-23, t$_R$=12.08 min, >99% pure.

Methyl(3,17β-dihydroxyestra-1,3,5(10)-estratrien-15α-yl)formate (49, E15-1,1). A solution of 41.8 mg (0.132 mmol) of 48, 1 drop of concentrated H$_2$SO$_4$ in MeOH (2 mL) was heated at 60° C. in a sealed vial for 75 h. The reaction mixture was poured into saturated aqueous NaHCO$_3$ (50 mL) and extracted with EtOAc (3×, 70 mL). Combined organic extracts were dried over Na$_2$SO$_4$ and concentrated in vacuo giving a yellow oil. Purification of the residue by flash chromatography on a 2×17 cm column of silica gel using 1:1 hexanes/EtOAc as eluent gave 21.2 mg of 49 as a white solid. Further purification of this material by HPLC with system H-21 ($t_R$=12–14 min) gave 19.1 mg (44%) of 49. Crystallization from acetone-petroleum ether gave 16.9 mg (39%) of 49 as white needles for bioassay. Data for 49: TLC, T-2, $R_f$ 0.45; $^1$H NMR (400 MHz, CDCl$_3$) δ 0.83 (s, 3H, H-18), 3.71 (s, 3H, OCH$_3$), 3.93 (t, 1H, J=8.8 Hz, H-17α), 4.56 (br s, 1H, OH), 6.55 (d, 1H, J=2.8 Hz, H-4), 6.63 (dd, 1H, J=8.6, 2.8 Hz, H-2), 7.16 (d, 1H, J=8.6 Hz, H-1); HRMS (ES$^+$) calcd for C$_{20}$H$_{26}$O$_4$Na (M+Na$^+$) m/e 353.1729, found m/e 353.1737; HPLC system H-15, $t_R$=13.21 min, and system H-25, $t_R$=8.15 min, >99% pure.

Ethyl(3,17β-dihydroxyestra-1,3,5(10)-trien-15α-yl)formate (50, E15-1,2). Compound 50 was prepared by esterification of 48 (43.1 mg, 0.136 mmol) with EtOH as described for 49. Purification of the residue by flash chromatography on a 2×17 cm column of silica gel using 1:1 hexanes/EtOAc as eluent followed by HPLC with system H-21 gave 23.3 mg (50%) of 50. Crystallization from acetone-petroleum ether gave 18.6 mg (40%) of 50 as white needles for bioassay. Data for 50: TLC, T-2, $R_f$ 0.375; $^1$H NMR (400 MHz, CDCl$_3$) δ 0.83 (s, 3H, H-18), 1.29 (t, 3H, J=7.1 Hz, —OCH$_2$CH$_3$), 3.93 (t, 1H, J=8.9 Hz, H-17α), 4.17 (q, 2H, J=7.2 Hz, —OCH$_2$CH$_3$), 4.59 (br s, 1H, OH), 6.55 (d, 1H, J=2.7 Hz, H-4), 6.63 (dd, 1H, J=8.6, 2.7 Hz, H-2), 7.16 (d, 1H, J=8.6 Hz, H-1); HRMS (ES$^+$) calcd for C$_{21}$H$_{28}$O$_4$Na (M+Na$^+$) m/e 367.1885, found m/e 367.1882; HPLC system H-15, $t_R$=12.55 min, and system H-25, $t_R$=11.77 min, >99% pure.

2'-Fluoroethyl(3,17β-dihydroxyestra-1,3,5(10)-trien-15α-yl)formate (51, E15-1,2F$_1$). Compound 51 was prepared by esterification of 48 (83.9 mg, 0.265 mmol) with 2'-fluoroethanol as described for 49. Purification of the residue by flash chromatography on a 3×21 cm column of silica gel using 1:1 hexanes/EtOAc as eluent gave 33.6 mg of 51. Further purification by HPLC with system H-21 in 3 portions gave 29.1 mg (29%) of 51 as a white solid. Crystallization from acetone-petroleum ether gave 24.9 mg (25%) of 51 as white needles for bioassay. Data for 51: TLC, T-3, $R_f$ 0.65; $^1$H NMR (400 MHz, CDCl$_3$) δ 0.84 (s, 3H, H-18), 3.93 (t, 1H, J=8.8 Hz, H-17α), 4.36 (m, 2H, —OCH$_2$CH$_2$F), 4.63 (dt, 2H, J=47.5, 4.1, 4.1 Hz, —OCH$_2$CH$_2$F), 6.55 (d, 1H, J=2.7 Hz, H-4), 6.63 (dd, 1H, J=8.3, 2.7 Hz, H-2), 7.16 (d, 1H, J=8.3 Hz, H-1); HRMS (ES$^+$) calcd for C$_{21}$H$_{27}$FO$_4$Na (M+Na$^+$) m/e 385.1791, found m/e 385.1791; HPLC system H-15, $t_R$=12.69 min, and system H-25, $t_R$=9.37 min, >99% pure.

Propyl(3,17β-dihydroxyestra-1,3,5(10)-trien-15α-yl)formate (52, E15-1,3). Compound 52 was prepared by esterification of 48 (33.9 mg, 0.107 mmol) with nPrOH as described for 49. Purification of the residue by flash chromatography on a 2×17 cm column of silica gel using 1:1 hexanes/EtOAc as eluent gave 21.9 mg of 52. Further purification by HPLC with system H-21 in 3 portions gave 22.3 mg (58%) of 52 as a white solid. Crystallization from acetone-petroleum ether gave 12 mg (31%) of 52 as white needles. Data for 52: TLC, T-3, $R_f$ 0.64; $^1$H NMR (400 MHz, CDCl$_3$) δ 0.83 (s, 3H, H-18), 0.98 (t, 3H, J=7.5 Hz, OCH$_2$CH$_2$CH$_3$), 3.93 (t, 1H, J=8.6 Hz, H-17α), 4.05–4.08 (m, 2H, OCH$_2$CH$_2$CH$_3$), 6.54 (d, 1H, J=2.7 Hz, H-4), 6.63 (dd, 1H, J=8.2, 2.7 Hz, H-2), 7.20 (d, 1H, J=8.2 Hz, H-1); HRMS (ES$^+$) calcd for C$_{22}$H$_{30}$O$_4$Na (M+Na$^+$) m/e 381.2042, found m/e 381.2034; HPLC system H-15, $t_R$=11.97 min, and system H-25, $t_R$=19.35 min, >99% pure.

Isopropyl(3,17β-dihydroxyestra-1,3,5(10)-trien-15α-yl)formate (53, E15-1,3i). Compound 53 was prepared by esterification of 48 (34.6 mg, 0.109 mmol) with iPrOH as described for 49. Purification of the residue by flash chromatography on a 2×17 cm column of silical gel using 1:1 hexanes/EtOAc gave 21.3 mg of 53. Further purification by HPLC with system H-21 in 4 portions gave 16 mg (41%) of 53 as a white solid. Crystallization from Et$_2$O-petroleum ether gave 13.6 mg (35%) of 53 as white needles. Data for 53: TLC, T-3, $R_f$ 0.74; $^1$H NMR (400 MHz, CDCl$_3$) δ 0.82 (s, 3H, H-18), 1.26 (d, 6H, J=6.3 Hz, —OCH(CH$_3$)$_2$), 3.91 (t, 1H, J=8.5 Hz, H-17α), 5.04 (septet, 1H, J=6.3 Hz, —OCH(CH$_3$)$_2$), 6.55 (d, 1H, J=2.6 Hz, H-4), 6.63 (dd, 1H, J=8.5, 2.6 Hz, H-2), 7.16 (d, 1H, J=8.5 Hz, H-1); HRMS (ES$^+$) calcd for C$_{22}$H$_{30}$O$_4$Na (M+Na$^+$) m/e 381.2042, found m/e 381.2038; HPLC system H-16, $t_R$=11.3 min, and system H-28, $t_R$=11.4 min, >99% pure.

Butyl(3,17β-dihydroxyestra-1,3,5(10)-trien-15α-yl)formate (54, E15-1,4). Compound 54 was prepared by esterification of 48 (29.1 mg, 0.0920 mmol) with nBuOH as described for 49. Purification of the residue by flash chromatography on a 3×21 cm column of silica gel using 1:1 hexanes/EtOAc as eluent gave 16.2 mg of 54. Further purification by HPLC with system H-21 in 4 portions gave 10.5 mg (31%) of 54 as a white solid. Crystallization from Et$_2$O-petroleum ether gave 9.6 mg (28%) of 54 as white needles. Data for 54: TLC, T-3, $R_f$ 0.85; $^1$H NMR (400 MHz, CDCl$_3$) δ 0.83 (s, 3H, H-18), 0.96 (t, 3H, J=7.3 Hz, —OCH$_2$CH$_2$CH$_2$CH$_3$), 3.92 (t, 1H, J=8.8 Hz, H-17α), 4.11 (t, 2H, J=6.6 Hz, —OCH$_2$—), 6.55 (d, 1H, J=2.5 Hz, H-4), 6.63 (dd, 1H, J=8.6, 2.5 Hz, H-2), 7.16 (d, 1H, J=8.6 Hz, H-1); HRMS (ES$^+$) calcd for C$_{23}$H$_{32}$ONa (M+Na$^+$) m/e 395.2198, found m/e 395.2193; HPLC system H-15, $t_R$=14.78 min, and system H-25, $t_R$=32.53 min, >99% pure.

Ethyl(17β-hydroxy-3-methoxyestra-1,3,5(10)-trien-15α-yl)formate (55). A solution of 53.7 mg (0.144 mmol) of 50, 400 μL (6.40 mmol) of CH$_3$I, 96 mg (0.695 mmol) of K$_2$CO$_3$ in acetone (5 mL) was stirred at rt for 19 h then heated at 60° C. for 6 h. The reaction mixture was allowed to cool to rt, poured into H$_2$O (70 mL) and extracted with EtOAc (3×, 50 mL). Combined organic extracts were dried over Na$_2$SO$_4$ and concentrated in vacuo. Purification by flash chromatography on a 2×15 cm column of silica gel using 2:1 hexanes/EtOAc as eluent gave 55.7 mg (100%) of 55 TLC, T-2, $R_f$ 0.51.

Ethyl(3-methoxy-17β-(methoxymethoxy)estra-1,3,5(10)-trien-15α-yl)formate (56). A solution of 59.9 mg (0.155 mmol) of 55, 269 μL (1.55 mmol) of iPrEt$_2$N, 118 μL (1.55 mmol) of MOMCl in anhydrous toluene (2 mL) was stirred at rt for 22 h. The reaction mixture was poured into H$_2$O (70 mL) and extracted with CH$_2$Cl$_2$ (3×, 50 mL). Combined organic extracts were dried over Na$_2$SO$_4$ and concentrated in vacuo giving a yellow oil. Purification by flash chromatography on a 2×17 cm column of silica gel using 3:1 hexanes/EtOAc as eluent gave 53.7 mg (80%) of 56. Data for 56: TLC, T-2, $R_f$ 0.8; $^1$H NMR (500 MHz, CDCl$_3$) δ 0.85 (s, 3H, H-18), 1.29 (t, 3H, J=7.2 Hz, CH$_2$CH$_3$), 3.37 (s, 3H, —CH$_2$OCH$_3$), 3.77 (t, 1H, J=8.7 Hz, H-17α), 3.78 (s, 3H, ArOCH$_3$), 4.20–4.14 (m, 2H, —CH$_2$CH$_3$), 4.66 (s, 2H, OCH$_2$O), 6.61 (d, 1H, J=2.8 Hz, H-4), 6.71 (dd, 1H, J=8.8, 2.8 Hz, H-2), 7.21 (d, 1H, J=8.8 Hz, H-1).

15α-Hydroxymethyl-3-methoxy-17β-(methoxymethoxy)estra-1,3,5(10)-triene (57). A solution of 53.7 mg (0.125 mmol) of 56 in anhydrous Et$_2$O (2 mL) was stirred at rt as 47.3 mg (1.25 mmol) of LiAlH$_4$ was added and reaction was stirred at rt for 2 h. The reaction mixture was poured into saturated Na—K tartrate (100 mL) and extracted with EtOAc (3×, 70 mL). Combined organic extracts were dried over $Na_2SO_4$ and concentrated in vacuo giving 47.1 mg (87%) of 57 as a clear colorless oil which was a single isomer as judged by $^1H$ NMR and used without further purification in the next step. Data for 57: TLC, T-2, $R_f$ 0.31; $^1H$ NMR (400 MHz, $CDCl_3$) δ 0.88 (s, 3H, H-18), 1.05 (t, 1H, J=10.6 Hz, H-14), 3.38 (s, 3H, —$CH_2OCH_3$), 3.42 (dd, 1H, J=10.3, 8.2 Hz, $CH_2OH$), 3.60 (t, 1H, J=8.9 Hz, H-17α), 3.78 (s, 3H, $ArOCH_3$), 3.89 (dd, 1H, J=10.3, 3.2 Hz, —$CH_2OH$), 4.66 & 4.69 (AB quartet, 2H, $J_{AB}$=6.5 Hz, $OCH_2O$), 6.62 (d, 1H, J=2.6 Hz, H-4), 6.72 (dd, 1H, J=8.7, 2.6 Hz, H-2), 7.22 (d, 1H, J=8.7 Hz, H-1).

3-Methoxy-17β-methoxymethoxy-15α-toluenesulfonyloxymethylestra-1,3,5(10)-triene (58). A solution of 47.1 mg (0.109 mmol) of 57, 457 mg (2.39 mmol) of pTsCl in pyridine (7 mL) was allowed to stand in a sealed vial at 4° C. for 24 h. The reaction mixture was poured into $H_2O$ (100 mL) and extracted with $CH_2Cl_2$ (3×, 70 mL). Combined organic extracts were dried over $Na_2SO_4$ and concentrated in vacuo giving a yellow oil. Purification by flash chromatography on a 2×17 cm column of silica gel using 3:1 hexanes/EtOAc as eluent gave 60 mg (94%) of 58. Data for 58: TLC, T-2, $R_f$ 0.73; $^1H$ NMR (400 MHz, $CDCl_3$) δ 0.82 (s, 3H, H-18), 0.99 (t, 1H, J=10.9 Hz, H-14), 2.45 (s, 3H, $ArCH_3$), 3.35 (s, 3H, $CH_2OCH_3$), 3.52 (t, 1H, J=8.8 Hz, H-17α), 3.78 (s, 3H, $ArOCH_3$), 3.80 (dd, 1H, J=9.5, 8.0 Hz, $CH_2OH$), 4.26 (dd, 1H, J=9.5, 3.1 Hz, $CH_2OH$), 4.61 (s, 2H, $OCH_2O$), 6.60 (d, 1H, J=2.7 Hz, H-4), 6.71 (dd, 1H, 8.6, 2.7 Hz, H-2), 7.19 (d, 1H, J=8.6 Hz, H-1), 7.37 (d, 2H, J=8.1 Hz, Ar—H), 7.82 (d, 2H, J=8.1 Hz, Ar—H).

3-Methoxy-17β-methoxymethoxy-15α-methylestra-1,3,5(10)-triene (59). A solution of 15.8 mg (0.0269 mmol) of 58 in anhydrous THF (500 μL) was stirred at rt as 108 μL of a 1 M solution of $LiEt_3BH$ in THF (0.108 mmol) was added and the reaction was stirred and heated at 65° C. for 5 h then quenched at rt with EtOH (1 mL). To the reaction mixture was added diglyme (2 mL), 48 mg (0.431 mmol) $Et_3NO$ and the reaction was stirred and heated at 150° C. for 1 h allowing the THF to evaporate. The reaction mixture was allowed to cool to rt, poured into $H_2O$ (50 mL) and extracted with EtOAc (3×, 50 mL). Combined organic extracts were washed with 10% $Na_2S_2O_5$ (30 mL), $H_2O$ (30 mL), dried over $Na_2SO_4$ and concentrated in vacuo giving a colorless oil. Purification by flash chromatography on a 2×17 cm column of silica gel using 4:1 hexanes/EtOAc as eluent gave 9 mg (97%) of 59. Data for 59: TLC, T-1, $R_f$ 0.73; $^1H$ NMR (400 MHz, $CDCl_3$) δ 0.86 (s, 3H, H-18), 0.90 (t, 1H, J=10.2 Hz, H-14), 1.12 (d, 3H, J=6.2 Hz, 15α-$CH_3$), 3.38 (s, 3H, $CH_2OCH_3$), 3.64 (t, 1H, J=8.6 Hz, H-17α), 3.79 (s, 3H, $ArOCH_3$), 4.65–4.67 (AB quartet, 2H, $J_{AB}$=6.6 Hz, $OCH_2O$), 6.62 (d, 1H, J=2.8 Hz, H-4), 6.72 (dd, 1H, J=8.6, 2.8 Hz, H-2), 7.22 (d, 1H, J=8.6 Hz, H-1).

3-Methoxy-15α-methylestra-1,3,5(10)-trien-17β-ol (60). A solution of 9 mg (0.026 mmol) of 59, 5 μL of concentrated HCl, in MeOH (2 mL) was stirred at rt for 15 min then heated at 60° C. for 30 min. Another 25 mL of concentrated HCl was added and the reaction was stirred at 60° C. for 1 h. The reaction mixture was poured into saturated aqueous $NaHCO_3$ (5 mL) and extracted with EtOAc (3×, 5 mL). Combined organic extracts were dried over $Na_2SO_4$ and concentrated in vacuo giving a clear yellow oil. Purification by flash chromatography on 2×17 cm column of silica gel using 2:1 hexanes/EtOAc as eluent gave 7.3 mg (93%) of $60^{25}$. Data for 60: TLC, T-1, $R_f$ 0.31; $^1H$ NMR (400 MHz, $CDCl_3$) δ 0.82 (s, 3H, H-18), 0.90 (t, 1H, J=10.2 Hz, H-14) 1.13 (d, 3H, J=6.3 Hz, 15α-$CH_3$), 3.76 (t, 1H, J=8.7 Hz, H-17α), 3.79 (s, 3H, $ArOCH_3$), 6.63 (d, 1H, J=2.7 Hz, H-4), 6.72 (dd, 1H, J=8.6, 2.7 Hz, H-2), 7.22 (d, 1H, J=8.6 Hz, H-1).

Diethyl-(3-benzyloxy-17-oxoestra-1,3,5(10)-trien-15α-yl)malonate (61α) & Diethyl-(3-benzyloxy-17-oxoestra-1, 3,5(10)-trien-15β-yl)malonate (61β). A suspension of 46.1 mg of NaH (76.8 mg of 60% dispersion in oil, washed with hexanes, 1.92 mmol) in anhydrous THF (1 mL) was stirred at rt as 264 μL (1.74 mmol) of diethyl malonate was added and the reaction mixture was stirred at rt for 30 min. To this was added a solution of 312.5 mg (0.872 mmol) of 44 in THF (2 mL) and the reaction was stirred at rt for 1.5 h, poured into saturated aqueous $NH_4Cl$ and extracted with $CH_2Cl_2$ (3×, 30 mL). Combined organic extracts were dried over $Na_2SO_4$ and concentrated in vacuo giving a slightly yellow oil. Purification by flash chromatography on a 3×21 cm column of silica gel using 3:1 hexanes/EtOAc as eluent gave 392 mg (87%) of 61 as an inseparable 5:1 mixture of 15α and 15β epimers. Data for 61α: TLC, T-1, $R_f$ 0.45; $^1H$ NMR (400 MHz, $CDCl_3$) δ 1.01 (s, 3H, H-18), 1.27 (t, 3H, J=7.1 Hz, $OCH_2CH_3$), 1.29 (t, 3H, J=7.1 Hz, $OCH_2CH_3$), 4.01 (d, 1H, J=4.0 Hz, $HC(CO_2Et)_2$), 4.22 (m, 4H, O $CH_2CH_3$), 5.04 (s, 2H, benzylic-H), 6.72 (d, 1H, J=2.6 Hz, H-4), 6.80 (dd, 1H, J=8.7, 2.6 Hz, H-2), 7.21 (d, 1H, J=8.7 Hz, H-1), 7.33–7.44 (m, 5H, Ar—H); Data attributed to 61β: $^1H$ NMR (400 MHz, $CDCl_3$) δ 1.21 (s, 3H, H-18), 3.72 (d, 1H, J=3.5 Hz, $HC(CO_2Et)_2$).

(3-Benzyloxy-17-oxoestra-1,3,5(10)-trien-15α-yl)malonic acid (62). A solution of 392 mg (0.756 mmol) of 61, 2 g NaOH in 30 mL of EtOH and 10 mL of $H_2O$ was stirred at rt for 17 h. The reaction mixture was concentrated to about 15 mL and poured into 100 mL $H_2O$ and washed with $Et_2O$ (1×, 20 mL). The aqueous phase was adjusted to pH 2 with concentrated HCl and extracted with EtOAc (3×, 70 mL). Combined organic extracts were washed with saturated aqueous NaCl (1×, 50 mL), dried over $Na_2SO_4$ and concentrated in vacuo giving 297 mg (85%) of 62 as a white solid. It was one isomer by inspection of the $^1H$ NMR and it was used without purification in the next step. Data for 62: TLC, T-3, $R_f$ 0.08; $^1H$ NMR (400 MHz, $CDCl_3$) δ 1.03 (s, 3H, H-18), 4.14 (d, 1H, J=3.7 Hz, $HC(CO_2H)$, 5.04 (s, 2H, benzylic-H), 6.72 (s, 1H, J=2.7 Hz, H-4), 6.80 (dd, 1H, J=8.7, 2.7 Hz, H-2), 7.20 (d, 1H, J=8.7 Hz, H-1), 7.33–7.45 (m, 5H, Ar—H).

(3-Benzyloxy-17-oxoestra-1,3,5(10)-trien-15α-yl)acetic acid (63). A solution of 297 mg (0.642 mmol) of 62 crude in 10 mL of 2-methoxyethyl ether was stirred and heated at 162° C. for 15 min. The reaction mixture was allowed to cool to rt, poured into $H_2O$ (100 mL) and extracted with EtOAc (3×, 70 mL). Combined organic extracts were washed with 10% $Na_2S_2O_5$ and concentrated in vacuo giving a yellow oil which was used without purification in the next step. Data for 63: TLC, T-3, $R_f$ 0.58; $^1H$ NMR (400 MHz, $CDCl_3$) δ 1.01 (s, 3H, H-18), 5.04 (s, 2H, benzylic-H), 6.72 (d, 1H, J=2.6 Hz, H-4), 6.81 (dd, 1H, J=8.5, 2.6 Hz, H-2), 7.22 (d, 1H, J=8.5 Hz, H-1), 7.30–7.45 (m, 5H, Ar—H).

(3-Benzyloxy-17β-hydroxyestra-1,3,5(10)-trien-15α-yl) acetic acid (64). A solution of crude 63, 97 mg (2.57 mmol) of $NaBH_4$ in EtOH (20 mL) was stirred at rt for 22 h. The reaction mixture was poured into saturated $Na_2CO_3$ (70 mL) and washed with $Et_2O$ (1×, 50 mL). The aqueous phase was adjusted to pH 1 and extracted with EtOAc (2×, 70 mL). Combined organic extracts were washed with $H_2O$ (2×, 50 mL), dried over $Na_2SO_4$ and concentrated in vacuo giving 220 mg (82%, 2 steps) of 64 as a white solid. Data for 64:

TLC, T-3, R_f 0.46; ¹H NMR (400 MHz, CDCl₃) δ 0.85 (s, 3H, H-18), 1.03 (t, 1H, J=10.5 Hz, H-14), 3.77 (t, 1H, J=8.9 Hz, H-17α), 5.04 (s, 2H, benzylic-H), 6.71 (d, 1H, J=2.9 Hz, H-4), 6.80 (dd, 1H, J=8.3, 2.9 Hz, H-2), 7.22 (d, 1H, J=8.3 Hz, H-1), 7.33–7.45 (m, 5H, Ar—H).

(3,17β-Dihydroxyestra-1,3,5(10)-trien-15α-yl)acetic acid (65, E15-2,0). Compound 65 was prepared from 64 (220 mg, 0.523 mmol) as described for 48 giving a yellow oil which crystallized on standing. Further purification of 33.9 mg of this material by HPLC with system H-20 gave 15.8 mg of 65 for bioassay. Data for 65: TLC, T-3, R_f 0.33; ¹H NMR (400 MHz, DMSO-d₆) δ 0.70 (s, 3H, H-18), 0.91 (t, 1H, J=9.9 Hz, H-14), 3.51 (t, 1H, J=8.9 Hz, H-17α), 6.41 (d, 1H, J=2.7 Hz, H-4), 6.50 (dd, 1H, J=8.6, 2.7 Hz, H-2), 7.04 (d, 1H, J=8.6 Hz, H-1); HRMS (ES⁺) calcd for $C_{20}H_{26}O_4Na$ (M+Na⁺) m/e 353.1729, found m/e 353.1731; HPLC system H-20, $t_R$=13.57 min, and system H-23, $t_R$=21.28 min, >99% pure.

Methyl(3,17β-dihydroxyestra-1,3,5(10)-trien-15α-yl)acetate (66, E15-2,1). To a solution of 50.6 mg of 65 (0.153 mmol) in MeOH (2.5 mL) was added SOCl₂ (17 μL). The solution was stirred and heated at 40° C. for 3 h and then evaporated under an N₂ stream, diluted with EtOAc (20 mL), washed with saturated aqueous NaHCO₃ (20 mL). The organic phase was washed with H₂O, dried over Na₂SO₄ and evaporated. Purification by flash chromatography on a 2×17 cm column of silica gel using 2:1 EtOAc/hexanes as eluent gave 38.5 mg of 66. Further purification by HPLC with system H-21 gave 27.9 mg of 66. Crystallization from Et₂O-petroleum ether gave 22.4 mg (43%) of 66 as white needles. Data for 66: TLC, T-3, R_f 0.61; ¹H NMR (400 MHz, CDCl₃) δ 0.84 (s, 3H, H-18), 1.00 (t, 1H, J=10.5 Hz, H-14), 3.69 (s, 3H, OCH₃), 3.74 (t, 1H, J=8.4 Hz, H-17α), 6.55 (d, 1H, J=2.6 Hz, H-4), 6.64 (dd, 1H, J=8.5, 2.6 Hz, H-2), 7.17 (d, 1H, J=8.5 Hz, H-1); HRMS (ES⁺) calcd for $C_{21}H_{28}O_4Na$ (M+Na⁺) m/e 367.1885, found m/e 367.1872; HPLC system H-21, $t_R$=16.5 min, and system H-25, $t_R$=10.78 min, >99% pure.

Ethyl(3,17β-dihydroxyestra-1,3,5(10)-trien-15α-yl)acetate (67, E15-2,2). Compound 67 was prepared from 65 (41.9 mg, 0.127 mmol) with EtOH as described for 66. Purification by flash chromatography on a 2×17 cm column of silica gel using 2:1 EtOAc/hexanes as eluent gave 36.7 mg of 67. Further purification by HPLC with system H-21 gave 36 mg of 67. Crystallization from Et₂O-petroleum ether gave 26.6 mg (58%) of 67 as fine needles. Data for 67: TLC, T-3, R_f 0.67; ¹H NMR (400 MHz, CDCl₃) δ 0.84 (s, 3H, H-18), 1.01 (t, 1H, J=10.5 Hz, H-14), 1.28 (t, 3H, J=7.0 Hz, CH₂CH₃), 3.74 (br t, 1H, J=8.5 Hz, H-17α), 4.15 (q, 1H, J=7.0 Hz, CH₂CH₃), 6.56 (d, 1H, J=2.7 Hz, H-4), 6.64 (dd, 1H, J=8.5, 2.7 Hz, H-2), 7.17 (d, 1H, J=8.5 Hz, H-1); HRMS (ES⁺) calcd for $C_{22}H_{30}O_4Na$ (M+Na⁺) m/e 381.2042, found m/e 381.2028; HPLC system H-21, $t_R$=15.70 min, and system H-25, $t_R$=16.38 min, >99% pure.

3-Benzyloxy-17β-hydroxyestsra-1,3,5(10)-trien-15α-yl) acetaldehyde (68). A solution of 10 mg (0.0279 mmol) of 67 in anhydrous toluene (500 μL) was stirred at −60° C. as 200 μL (0.3 mmol) of a 1.5 M solution of DIBAL in toluene was added. The reaction mixture was stirred at −60° C. for 1.5 h, poured into H₂O (3 mL) and extracted with EtOAc (2×, 3 mL). Combined organic extracts were dried over Na₂SO₄ and concentrated in vacuo giving a clear colorless oil. Purification by flash chromatography on a 1×17 cm column of silica gel using 2:1 EtOAc/hexanes gave 1.8 mg (20%) of 68. Data for 68: TLC, T-2, R_f 0.2; ¹H NMR (500 MHz, CDCl₃) δ0.85 (s, 3H, H-18), 1.05 (t, 1H, J=10.5 Hz, H-14), 3.75 (br t, 1H, J=9.7 Hz, H-17α), 4.53 (s, 1H, OH), 6.56 (d, 1H, J=2.8 Hz, H-4), 6.64 (dd, 1H, J=8.5, 2.8 Hz, H-2), 7.17 (d, 1H, J=8.5 Hz, H-1), 9.79 (d, 1H, J=1.6 Hz, CHO).

15α-Allylestra-1,3,5(10)-trien-3,17β-diol (69). A solution of 1.8 mg (0.0057 mmol) of 68 in anhydrous THF (500 μL) was stirred at 0° C. as 110 μL (0.048 mmol) of Nystead reagent and 1 μL of BF₃.OEt₂ was added. The reaction mixture was allowed to warm to rt, stirred for 2 h, transferred to 1N HCl (3 mL) and extracted with EtOAc (3×, 2 mL). Combined organic extracts were dried over Na₂SO₄ and concentrated in vacuo giving a clear colorless oil. Purification by flash chromatography on a 1×12 cm column of silica gel using 2:1 hexanes/EtOAc as eluent gave 1 mg (55%) of 69.³⁰ Data for 69: TLC, T-2, R_f 0.54; ¹H NMR (500 MHz, Acetone-d₆) δ 0.83 (s, 3H, H-18), 1.02 (t, 1H, J=10.3 Hz, H-14), 3.63 (t, 1H, J=8.9 Hz, H-17α), 4.97 (d, 1H, J=10.5 Hz, =CH₂), 5.03 (d, 1H, J=17.1 Hz, =CH₂), 5.81–5.90 (m, 1H, —CH=CH₂), 6.51 (d, 1H, J=2.6 Hz, H-4), 6.59 (dd, 1H, J=8.5, 2.6 Hz, H-2), 7.10 (d, 1H, J=8.5 Hz, H-1).

17α-Allyl-3-benzyloxyestra-1,3,5(10),15-tetraen-17β-ol (70). A solution of 477 mg (1.33 mmol) of 44 in anhydrous THF (5.15 mL) was stirred at 0° C. as 1.99 mL (3.99 mmol) of a 2 M solution of allylmagnesium chloride in THF was added dropwise slowly over 10 min. The reaction mixture was stirred at 0° C. for 3 h, poured into saturated aqueous NH₄Cl (70 mL) and extracted with EtOAc (3×, 70 mL). Combined organic extracts were washed with 10% Na₂S₂O₅ (30 mL), H₂O (50 mL), dried over Na₂SO₄ and concentrated in vacuo giving a white solid. Purification by flash chromatography on a 3×21 cm column of silica gel using 3:1 hexanes/EtOAc as eluent gave 389 mg (73%) of 70 as a white solid. Data for 70: TLC, T-1, R_f 0.61; ¹H NMR (400 MHz, CDCl₃) δ 0.96 (s, 3H, H-18), 5.05 (s, 2H, benzylic-H), 5.16–5.20 (m, 2H, =CH₂), 5.67 (dd, 1H, J=6.0, 3.2 Hz, H-15), 5.90–5.98 (m, 1H, —HC=), 5.99 (dd, 1H, J=6.0, 1.6 Hz, H-16), 6.74 (d, 1H, J=2.7 Hz, H-4), 6.80 (dd, 1H, J=8.6, 2.7 Hz, H-2), 7.21 (d, 1H, J=8.5 Hz, H-1), 7.31–7.45 (m, 5H, Ar—H).

15α-Allyl-3-benzyloxyestra-1,3,5(10)-trien-17-one (71). A 556 mg portion (4.85 mmol) of a 35% oil dispersion of KH was washed with hexanes and suspended in anhydrous THF (2 mL). To this was added a solution of 389 mg (0.971 mmol) of 70 and 1.28 g (4.85 mmol) of 18-crown-6 in THF (6 mL). The reaction mixture was stirred at rt for 3 h, transferred dropwise to EtOH (10 mL), diluted with saturated aqueous NH₄Cl (70 mL) and extracted with CH₂Cl₂ (3×, 70 mL). Combined organic extracts were washed with 10% Na₂S₂O₅ (30 mL), H₂O (30 mL), dried over Na₂SO₄ and concentrated in vacuo giving an orange oil. Purification by flash chromatography on a 3×21 cm column of silica gel using 4:1 hexanes/EtOAc as eluent gave 311 mg (80%) of 71 as a white solid. Data for 71: TLC, T-1, R_f 0.37; ¹H NMR (400 MHz, CDCl₃) δ 0.99 (s, 3H, H-18), 1.36 (t, 1H, J=10.7 Hz, H-14), 5.01–5.05 (m, 2H, =CH₂), 5.05 (s, 2H, benzylic-H), 5.74–5.85 (m, 1H, —HC=), 6.73 (d, 1H, J=2.6 Hz, H-4), 6.80 (dd, 1H, J=8.7, 2.8 Hz, H-2), 7.22 (d, 1H, J=8.7 Hz, H-1), 7.33–7.45 (m, 5H, Ar—H).

15α-Allyl-3-benzyloxyestra-1,3,5(10)-trien-17β-ol (72). A solution of 341 mg (0.850 mmol) of 71, 129 mg (3.40 mmol) of NaBH₄ in THF (9 mL) with 37 drops of H₂O was stirred at rt for 3 h, poured into saturated aqueous NH₄Cl (50 mL) and extracted with EtOAc (3×, 50 mL). Combined organic extracts were washed with 10% Na₂S₂O₅ (30 mL), H₂O (30 mL), dried over Na₂SO₄ and concentrated in vacuo giving a yellow oil. Purification by flash chromatography on a 3×21 cm column of silica gel using 2:1 hexanes/EtOAc as eluent gave 311 mg (91%) of 72. Data for 72: TLC, T-1, R_f 0.37; $^1$H NMR (500 MHz, CDCl$_3$) δ 0.83 (s, 3H, H-18), 1.02 (t, 1H, J=10.3 Hz, H-14), 3.70 (t, 1H, J=9.2 Hz, H-17α), 5.01–5.06 (m, 2H, =CH$_2$), 5.04 (s, 2H, benzylic-H), 5.78–5.86 (m, 1H, —CH=), 6.72 (d, 1H, J=2.7 Hz, H-4), 6.79 (dd, 1H, J=8.6, 2.7 Hz, H-2), 7.22 (d, 1H, J=8.6 Hz, H-1), 7.31–7.44 (m, 5H, Ar—H).

(15α-Allyl-3-benzyloxyestra-1,3,5(10)-trien-17β-yl)acetate (73). A solution of 311 mg (0.770 mmol) of 72, 2 mL of Ac$_2$O in pyridine (4 mL) was stirred at rt for 17 h. The reaction mixture was poured into H$_2$O (70 mL) and extracted with CH$_2$Cl$_2$ (3×, 50 mL). Combined organic extracts were dried over Na$_2$SO$_4$ and concentrated in vacuo giving a yellow oil. Purification by flash chromatography on a 3×21 cm column of silica gel using 5:1 hexanes/EtOAc as eluent gave 323 mg (94%) of 73. Data for 73: TLC, T-4, R$_f$ 0.45; $^1$H NMR (400 MHz, CDCl$_3$) δ 0.89 (s, 3H, H-18), 1.11 (t, 1H, J=10.2 Hz, H-14), 2.07 (s, 3H, OAc), 4.69 (t, 1H, J=8.8 Hz, H-17α), 5.01–5.07 (m, 2H, =CH$_2$), 5.04 (s, 2H, benzylic-H), 5.76–5.87 (m, 1H, —HC=), 6.71 (d, 1H, J=2.7 Hz, H-4), 6.79 (dd, 1H, J=8.6, 2.7 Hz, H-2), 7.21 (d, 1H, 8.6 Hz, H-1), 7.31–7.45 (m, 5H, Ar—H).

(3-Benzyloxy-15α-(3'-hydroxypropyl)estra-1,3,5(10)-trien-17β-yl)acetate (74). A solution of 304 mg (0.685 mmol) of 73 in anhydrous THF (4.9 mL) was stirred at 0° C. as 890 μL (0.890 mmol) of a 1 M solution of BH$_3$-THF in THF was added dropwise. The reaction mixture was stirred at rt for 2 h, diluted with EtOH (2 mL) and diglyme (10 mL). To this was slowly added 396 mg (3.56 mmol) trimethylamine N-oxide dihydrate and the reaction was heated at 150° C. for 1 h allowing the THF to evaporate. The reaction was cooled to rt, poured into H$_2$O (100 mL) and extracted with EtOAc (3×, 70 mL). Combined organic extracts were washed with 10% Na$_2$S$_2$O$_5$ (60 mL), H$_2$O (60 mL), dried over Na$_2$SO$_4$ and concentrated in vacuo giving a yellow oil. Purification by flash chromatography on a 3×21 cm column of silica gel using 1.5:1 hexanes/EtOAc as eluent gave 261 mg (82%) of 74. Data for 74: TLC, T-3, R$_f$ 0.59; $^1$H NMR (400 MHz, CDCl$_3$) δ 0.88 (s, 3H, H-18), 1.06 (t, 1H, J=10.2 Hz, H-19), 2.07 (s, 3H, OAc), 3.66 (t, 2H, J=6.6 Hz, CH$_2$OH), 4.69 (t, 1H, J=8.6 Hz, H-17α), 5.04 (s, 2H, benzylic-H), 6.71 (d, 1H, J=2.9 Hz, H-4), 6.79 (dd, 1H, J=8.6, 2.9 Hz, H-2), 7.21 (d, 1H, J=8.6 Hz, H-1), 7.33–7.45 (m, 5H, Ar—H).

3-(17β-Acetoxy-3-benzyloxyestra-1,3,5(10)-trien-15α-yl)propanioc acid (75). A solution of 261 mg (0.564 mmol) 74 in acetone (35 mL) was stirred at 0° C. as 211 μL (0.564 mmol) of 2.64 M CrO$_3$—H$_2$SO$_4$32 in H$_2$O was added. The reaction mixture was stirred at 0° C. for 20 min, poured into 1:1 MeOH/H$_2$O (120 mL), concentrated to about 60 mL and extracted with EtOAc (3×, 80 mL). Combined organic extracts were washed with H$_2$O (20 mL), dried over Na$_2$SO$_4$ and concentrated in vacuo giving 213 mg of 75 as a yellow foam and was used in the next step without purification. Data for 75: TLC, T-3, R$_f$ 0.54; $^1$H NMR (400 MHz, CDCl$_3$) δ 0.88 (s, 3H, H-18), 1.07 (t, 1H, J=10.2 Hz, H-14), 2.06 (s, 3H, OAc), 4.68 (t, 1H, J=8.5 Hz, H-17α), 5.04 (s, 2H, benzylic-H), 6.71 (d, 1H, J=2.7 Hz, H-4), 6.79 (dd, 1H, J=8.6, 2.7 Hz, H-2), 7.21 (d, 1H, J=8.6 Hz, H-1), 7.31–7.45 (m, 5H, Ar—H).

3-(3-Benzyloxy-17β-hydroxyestra-1,3,5(10)-trien-15α-yl)propanoic acid (76). A solution of 213 mg (0.446 mmol) of 75 in 5% aqueous KOH (20 mL) and MeOH (20 mL) was stirred and heated at 55° C. for 3 h. The reaction mixture was allowed to cool to rt, poured into H$_2$O (70 mL), adjusted to pH 2 with 10% HCl and extracted with Et$_2$O (3×, 40 mL). Combined organic extracts were washed with 10% Na$_2$S$_2$O$_5$ (30 mL), H$_2$O (30 mL), dried over Na$_2$SO$_4$ and concentrated in vacuo giving a white foam. Purification by flash chromatography on a 2×15 cm column of silica gel using 0.5:5 EtOH/CHCl$_3$ gave 134 mg (55% 2 steps) of 76. Data for 76: TLC, T-3, R$_f$ 0.46; $^1$H NMR (500 MHz, CDCl$_3$) δ 0.82 (s, 3H, H-18), 1.00 (t, 1H, J=10.0 Hz, H-14), 3.73 (t, 1H, J=8.6 Hz, H-17α), 5.04 (s, 2H, benzylic-H), 6.72 (d, 1H, J=2.8 Hz, H-4), 6.79 (dd, 1H, J=8.5, 2.8 Hz, H-2), 7.22 (d, 1H, J=8.5 Hz, H-1), 7.21–7.44 (m, 5H, Ar—H).

3-(3,17β-Dihydroxyestra-1,3,5(10)-trien-15α-yl)propionic acid (77, E15-3,0). Compound 77 was prepared from 76 (104 mg, 0.239 mmol) as described for 48. The filtrate was concentrated in vacuo giving 82 mg (100%) of 77 as a yellow oil. HPLC purification of a 43.3 mg portion of this material using system H-22 gave 36.2 mg of 77 for bioassay. Data for 77: TLC, T-3, R$_f$ 0.44; $^1$H NMR (400 MHz, DMSO-d$_6$) δ 0.68 (s, 3H, H-18), 3.48 (t, 1H, J=8.7 Hz, H-17α), 6.41 (d, 1H, J=2.6 Hz, H-4), 6.50 (dd, 1H, J=8.6, 2.6 Hz, H-2), 7.04 (d, 1H, J=8.6 Hz, H-1); HRMS (ES$^+$) calcd for C$_{21}$H$_{28}$O$_4$Na (M+Na$^+$) m/e 367.1885, found m/e 367.1882; HPLC system H-17, t$_R$=11.2 min, and system H-23, t$_R$=32.9 min, >99% pure.

Methyl 3-(3,17β-dihydroxyestra-1,3,5(10)-trien-15α-yl) propionate (78, E15-3,1). Compound 78 was prepared from 77 (51.6 mg, 0.150 mmol) as described for 66. Purification by flash chromatography on a 2×17 cm column of silica gel using 1:1 hexanes/EtOAc as eluent gave 48.5 mg of 78. Further purification by HPLC with system H-21 gave 42.3 mg. Crystallization from Et$_2$O-petroleum ether gave 31.2 mg (58%) of 78 as white needles. Data for 78: TLC, T-3, R$_f$ 0.62; $^1$H NMR (400 MHz, CDCl$_3$) δ 0.83 (s, 2H, H-18), 0.98 (t, 1H, J=10.2 Hz, H-14), 3.71 (s, 3H, OCH$_3$), 3.73 (t, 1H, J=8.5 Hz, H-17α), 6.57 (d, 1H, J=2.7 Hz, H-4), 6.65 (dd, 1H, J=8.3, 2.7 Hz, H-2), 7.18 (d, 1H, J=8.3 Hz, H-1); HRMS (ES$^+$) calcd for C$_{22}$H$_{30}$O$_4$Na (M+Na$^+$) m/e 381.2042, found m/e 381.2032; HPLC system H-18, t$_R$=8.5 min, and system H-25, t$_R$=14.45 min, >99% pure.

Ethyl 3-(3,17β-dihydroxyestra-1,3,5(10)-trien-15α-yl) propionate (79, E15-3,2). Compound 79 was prepared from 77 (51.65 mg,0.150 mmol) with EtOH as described for 66. Purification by flash chromatography on a 2×17 cm column of silica gel using 1:1 hexanes/EtOAc as eluent gave 48.7 mg. Further purification by HPLC with system H-21 gave 41.3 mg. Crystallization from Et$_2$O-petroleum ether gave 30.9 mg (56%) of 79 as white needles. Data for 79: TLC, T-3, R$_f$ 0.71; $^1$H NMR (400 MHz, CDCl$_3$) δ0.81 (s, 3H, H-18), 0.98 (t, 1H, J=10.1 Hz, H-14), 1.28 (t, 3H, J=7.1 Hz, OCH$_2$CH$_3$), 3.72 (t, 1H, J=8.4 Hz, H-17α), 4.12–4.18 (m, 2H, OCH$_2$CH$_3$), 6.56 (d, 1H, J=2.7 Hz, H-4), 6.63 (dd, 1H, J=8.3, 2.7 Hz, H-2), 7.17 (d, 1H, J=8.3 Hz, H-1); HRMS (ES$^+$) calcd for C$_{23}$H$_{32}$O$_4$Na (M+Na$^+$) m/e 395.2198, found m/e 395.2198; HPLC system H-18, t$_R$=8.2 min, and system H-25, t$_R$=21.98 min, >99% pure.

BIOLOGICAL DATA

Competitive Binding to the Estrogen Receptor ERα and ERβ. Binding affinities relative to E$_2$ were performed in incubations with the ER (ERα[33]) in uterine cytosol prepared from Sprague Dawley rats that had been castrated and 24 h prior to sacrifice. For assay, the cytosol was incubated with 1 nM [$^3$H]E$_2$ in the presence and absence of non-radioactive E$_2$, estrone (E$_1$), E16-1,2 and the E$_2$-carboxy analogs over a range of concentrations from $10^{-12}$ to $10^{-6}$ M. Incubations were carried out on ice overnight and bound radioactivity was separated from free by adsorption with dextran coated charcoal and quantified by counting.[34] The details of the assay are as we previously described.[20] Binding Affinity (RBA) was determined by analysis of the displacement curves by the curve-fitting program Prism. The results shown in Table 1 are from at least 3 separate experiments performed in duplicate[1]. A subset of the $E_2$-alkyl esters was also compared for binding to the ligand binding domain (LBD) of human ERα ($M_{250}$-$V_{595}$)[35] and human ERβ ($M^{214}$-$Q_{530}$).[36] The assay was performed in competition with [³H]$E_2$ in lysates of *Escherichia coli* in which the LBDs are expressed as described, with the exception that the incubation was performed overnight at 0–2° C.[37] The results, the average of 3 experiments, each performed in duplicate, as RBAs compared to $E_2$ and the ratio, RBA of ERα/ERβ, are shown in Table 2.

The results of the estrogen receptor assay are somewhat different from those we previously reported.[20] In those experiments the $K_d$ for $E_2$ averaged 1.75 nM and in these experiments 0.77 nM, whereas the $K_d$ for the other weaker estrogens such as estrone and the 16α-alkoxy analogs are as were reported. Thus, the RBA, which is relative to $E_2$, of the various analogs is decreased, while their ratio compared to estrone is unchanged. The reason for this shift in the measured $E_2$ affinity is unknown. Consequently, for comparative purposes, the receptor binding activity of estrone and E16-1,2 which were also run in parallel, are included in Table 1. The behavior of the estrogens in the Ishikawa bioassay did not change.

Estrogenic Potency in Ishikawa Cells. The estrogenic potency of the $E_2$-analogs was determined in an estrogen bioassay, the induction of alkaline phosphatase (AlkP) in human endometrial adenocarcinoma cells (Ishikawa) grown in 96-well microtiter plates as we have previously described.[38] In short, the cells are grown in phenol red free medium with estrogen depleted (charcoal stripped) bovine serum in the presence or absence of varying amounts of the steroids, across a dose range of at least 6 orders of magnitude. $E_2$, $E_1$ and E16-1,2 were included for comparison. After 3 days, the cells are washed, frozen and thawed, and then incubated with 5 mM p-nitrophenyl phosphate, a chromogenic substrate for the AlkP enzyme, at pH 9.8. To ensure linear enzymatic analysis, the plates are monitored kinetically for the production of p-nitrophenol at 405 nm. The relative stimulatory activity (RSA) represents the ratio of $EC_{50}$ of $E_2$ to that of the steroid analog×100, using the curve fitting program Prism to determine the $EC_{50}$. Each compound was analyzed in at least 3 separate experiments performed in duplicate.

In Vivo Estrogen Bioassays: Uterine Weight. Systemic estrogenic potency was determined by an uterotrophic assay in immature rats as described.[39] Female Sprague-Dawley rats, 22 days old, were injected subcutaneously daily for 3 days with a solution of 0.1 mL of the various steroids in sesame oil. Control animals received sesame oil. On the fourth day, the animals were killed, the uteri were removed, dissected, blotted and weighed. Except where noted, each compound was assayed in 2 separate experiments with n=5. The results comparing 100 μg (total dose) of the $E_2$-analogs to 5 ng of $E_2$ run concurrently are presented in Table 3.

In Vivo Estrogen Bioassays: Vaginal reductases. The estrogenic action of locally applied estrogens on the vagina was determined by measuring the induction of vaginal reductases.[40] Female CD-1 mice were ovariectomized and 1 week later the $E_2$-alkyl esters or $E_2$ were instilled into the vagina in 10 μL of sesame oil. (The details of the assay and the use of sesame oil to increase the $t_{1/2}$ of the steroid has been previously discussed.[20]) Briefly, the next morning 2,3,5-triphenyltetrazolium chloride is injected into the vagina and 30 minutes later the animals are euthanized and the vaginas removed, washed and extracted with ethanol/tetrachloroethylene (3:1). The formazan product in the organic extract is quantified at 500 nm. Except where noted, each compound was assayed on at least 2 separate occasions with at least 5–6 replicates each time. The results, compared to a 50 pg dose of $E_2$ are presented in Table 3.

Esterase. Esterase activity was measured in rat hepatic microsomes essentially using the conditions described[41] with some minor modifications. Briefly, rat hepatic microsomes were incubated with 50 μM E2-alkyl ester. Since the rates of reaction are widely different for the various esters, the incubation times and enzyme concentration were varied accordingly to obtain linear kinetics. In every experiment, E16-1,2 was run concurrently to normalize the rate of hydrolysis of each compound. At several appropriate time points during the incubation (37° C.), 100 μL aliquots were quenched with a solution of 2 μg of the internal standard, 6-ketoestradiol in 33 μL of $CH_3CN$, 33 μL of THF and 5 μL of glacial HOAc. The mixture was centrifuged and analyzed for the esterase-hydrolysis product (the corresponding $E_2$-carboxylic acid) by reversed phase HPLC: E16-1,0; E15-1,0; E15-2,0; and E15-3,0 by HPLC with system H-29. Peaks for the hydrolysis product (E16-1,0 $t_R$=10.7 min; E15-1,0 $t_R$=6.9 min; E15-2,0 $t_R$=9.9 min; E15-3,0 $t_R$=14 min;) and the internal standard ($t_R$=11.8 min for system H-29 and $t_R$=8.8 min for system H-30 were quantified at 280 nm on the HPLC UV detector. The UV absorbance was converted to nmoles of product by comparison to standard curves and corrected for recovery of the internal standard, 6-ketoestradiol. The velocity of the reaction for each ester, in nmol product/min/mg protein, was then normalized to the ester, E16-1,2 and is shown in Table 1 as relative hydrolytic activity (RHA) The enzymatic velocity for the hydrolysis of E16-1,2 was 2.34±0.8 (S.D.) nmol product/min/mg protein over the various experiments. All compounds were tested in triplicate in at least 2 separate experiments

TABLE 1

Estrogenic Properties of $E_2$-alkyl esters

| Compound[a] | | Estrogen Receptor (RBA[b]) | Ishikawa cell AlkP (RSA[c]) | Esterase (RHA[d]) |
|---|---|---|---|---|
| $E_2$ | | 100 | 100 | — |
| $E_1$ | | 9 ± 6 | 4 ± 2 | — |
| E16-1,2 | | 14 ± 4 | 9 ± 3 | 100 |
| E15-1,1 | (49) | 20 ± 10 | 11 ± 5 | 1.7 ± 0.1 |
| E15-1,2 | (50) | 25 ± 12 | 18 ± 10 | 2.3 ± 0.1 |
| E15-1,2$F_1$ | (51) | 8 ± 3 | 3 ± 0.2 | 4.5 ± 0.1 |
| E15-1,3 | (52) | 17 ± 5 | 2 ± 1 | 7.8 ± 0.4 |
| E15-1,3i | (53) | 5 ± 4 | 0.3 ± 0.06 | 0.4 ± 0.1 |
| E15-1,4 | (54) | 8 ± 2 | 0.7 ± 0.4 | 7 ± 0.5 |
| E15-2,0 | (65) | <0.1 | 0.2 ± 0.2 | — |
| E15-2,1 | (66) | 5 ± 3 | 1 ± 1 | 31 ± 6 |
| E15-2,2 | (67) | 2 ± 0 | 0.4 ± 0.5 | 71 ± 7 |
| E15-3,0 | (77) | 0 | 0 | — |
| E15-3,1 | (78) | 0.8 ± 0.1 | 0 | 248 ± 26 |
| E15-3,2 | (79) | <0.1 | 0 | 674 ± 14 |

Abbreviations are in FIG. 1, with examples as follows. E15-2,0 is the 15α-propionic acid analog of $E_2$. E15-2,1 is the methyl ester, 3i, the propyl ester, etc. The stereochemistry is not assigned in the abbreviations C-15 it is 15α, [b]RBA is the relative binding affinity in the ER assay, where $E_2$ = 100. [c]RSA is the relative stimulatory activity in the induction of alkaline phosphatase (AlkP) activity in the Ishikawa estrogen bioassay, where $E_2$ = 100. [d]RHA is the relative hydrolytic activity in the esterase assay with hepatic microsomes in comparison to E16-1,2. The dash (—) indicates not done. All values are ± SD.

TABLE 2

Binding of $E_2$-alkyl esters to the LBD of Human ERα and ERβ.

| cmpd | | ERα[a] | ERβ[a] | ERα/ERβ |
|---|---|---|---|---|
| $E_2$ | | 100 | 100 | 1 |
| E15-1,2 | (50) | 22 ± 5 | 7 ± 2 | 3 ± 0.6 |
| E-16-1,2 | | 27 ± 6 | 0.3 ± 0.1 | 95 ± 47 |

[a]RBA of the indicated ester compared to $E_2$. Values are ± SD. The inhibition of the binding of [$^3$H]$E_2$ in lysates of *E. coli* in which the LBD of human ERα and ERβ were separately expressed. Abbreviations are in Table 1. LBD is the ligand binding domain.

TABLE 3 in vivo Estrogenic Action. Systemic (uterotrophic) and Local (vaginal) Activity

| Compound | | Uterotrophic effect 100 μg dose (ng $E_2$ equivalent) | [a]Uterotrophic R.A × 10³ | Vaginal effect 50 ng dose (pg $E_2$ equivalent) | [a]Vaginal R.A × 10³ |
|---|---|---|---|---|---|
| E16-1,2F$_1$ | | 2[b] | 0.02 | 21[b] | 0.42 |
| E7β-1,1 | (8) | 10.5 (10–11) | 0.11 | 50[b] | 1.0 |
| E7α-1,2 | (9) | 4 (3.5–4.4) | 0.04 | 22[b] | 0.44 |
| E11-2,1 | (33) | 6.5[b] | 0.07 | 21[b] | 0.42 |
| E15-1,1 | (49) | n.s. (0–1.3) | n.s. | 19 (15–23) | 0.38 |
| E15-1,2 | (50) | n.s. (0.7–3) | n.s. | 21 (18–25) | 0.42 |

In the uterotrophic assay the results are compared to the effect of 5 ng (total dose administered over 3 days) of $E_2$ injected subcutaneously in immature rats; and in the vaginal assay the results are compared to 50 pg of $E_2$ administered vaginally to ovariectomized adult mice. In the uterotrophic assays n = 5, and in the vaginal assays n = 5–6. Values in brackets show the range.
[a]R.A. activity relative to $E_2$.
n.s. = not significantly different from the control. Except where noted, each compound was assayed in three different experiments.
[b]Data are from a single experiment.

RESULTS AND DISCUSSION

We synthesized carboxylic acid analogs of $E_2$ 15α- and its esters and evaluated them as "soft" estrogens in several different types of assays designed to measure their inherent estrogenic potency as well as to differentiate their systemic and local actions.

15α-Substitution. We synthesized a series of D-ring carboxylates and esters at C-15α. The E15-3 (propionate) esters are very poor ligands for the estrogen receptor and consequently they are devoid of estrogenic activity in the Ishikawa cell assay. While the C15-2 (acetate) analogs were somewhat better ligands for the estrogen receptor than the E15-3 esters, with RBAs for E15-2,1 and E15-2,2 of 5% and 2% respectively; their biological activity in the Ishikawa bioassay is low. The E15-1 compounds (formate) have very good estrogenic potential. The formate analog, E15-1,0, does not bind to the estrogen receptor, nor does it have estrogenic activity in the Ishikawa cell assay. However, as would be desired for "soft" hormones, the esters E15-1,1 and E15-1,2 are very potent ligands for estrogen receptor (RBA=20% and 25%) with very good activity in the Ishikawa cell assay (RSA=11% and 18%). However, the rate of enzymatic hydrolysis is relatively slow for both, (RHA: E15-1,1=1.7% and E15-1,2=2.3%). As with 16α-analogs, we attempted to increase the hydrolytic rate by introducing fluorine (E15-1,2F$_1$) or by lengthening the alcohol moiety of the ester (E15-1,3 and E15-1,4). While the hydrolytic rates do increase, the estrogenic activity of these 3 compounds decrease precipitously when compared to the methyl or ethyl esters. Steric factors are important determinants in the rate of enzymatic hydrolysis: the isopropyl ester, E15-1,3i, has an RHA=0.3%, which is much slower than the propyl ester, E15-1,3, RHA=7. Again, lengthening the carboxylic acid chain increases the rate of hydrolysis; compare the RHA of E15-3>E15-2>E15-1 esters containing the same alcohols. However, as discussed above, the esters in the E15-2 and E15-3 series have low affinity for the estrogen receptor and poor estrogenic action.

Binding to ERα and ERβ. In addition to the classical estrogen receptor, now called estrogen receptor α (ERα), there is another subtype of estrogen receptor, termed ERβ. These estrogen activated transcription factors are expressed differently in various tissues and although they both bind $E_2$ avidly, they have a somewhat different affinity for other estrogens.[33,42] Various substitutions at 16α- of $E_2$ have a profound differential affect on the binding of the two estrogen receptor subtypes, with preferential binding to ERα.[20,43] In this study we investigated the relative binding of a representative ethyl ester of the analog at 15α-(E15-1,2) to the ligand binding domain (LBD) of ERα and ERβ. For comparison, E16-1,2 which is ERαspecific,[20] was also included in these experiments. As can be seen in Table 2, E15-1,2 showed a small selectivity, about 3-fold for ERα. Again, E16-1,2 was a highly selective ligand with about a 95-fold preference for ERα.

in vivo Studies. Several of the analogs were tested for estrogenic potency in in vivo assays for systemic (uterotrophic assay) and local (vaginal assay) action. In both of these assays the esters were compared to $E_2$; 50 pg of $E_2$ in the vaginal assay (within the dose range that produces a linear response) and 5 ng of $E_2$ in the uterotrophic assay (the minimum dose that we found reproducibly produces a statistically significant uterine stimulation). The objective of this study was to determine which compounds show the greatest differential between local (high) and systemic (low) action. The results are in Table 3. The E15-1,1 and E15-1,2 analogs are estrogenic in vitro and in the vaginal assay (50 ng, equivalent to approximately 20 pg of $E_2$. However, neither of these 15α-substituted estrogens produced a statistically significant uterotrophic response at the 100 μg dose. Both were slightly estrogenic at a dose of 300 μg, producing a statistically significant stimulation (P<0.05); E15-1,1 and E15-1,2, equivalent to 4 and 5 ng of $E_2$ respectively. For comparative purposes, in one of the uterotrophic assays with E15-1,1 and E15-1,2 we included a 100 μg dose E16-1,2F$_1$ group. This compound showed the best differential in comparing local vs. systemic estrogenic effects in our previous study.[20] In this assay, 100 μg of E16-1,2F$_1$ produces a statistically significant (P<0.01) uterotrophic stimulation equivalent to 2 ng of $E_2$. This is approximately what was observed previously, although in those experiments the standard deviations were higher and the stimulation was not statistically significant.

Our previous studies showed that esters of carboxylic analogs of $E_2$ at C-16α that have high estrogenic potential (estrogen receptor binding and Ishikawa cell stimulation) and rapid esterase hydrolysis (E16-1,2 and E16-1,2F$_1$) generate a large differential between local and systemic estrogenic activity in vivo.[20]

However, the analogs E15-1,1 and E15-1,2 do not appear to behave according to this model. Both are highly potent estrogens in receptor binding and in the Ishikawa assay, more potent than either E1 or E16-1,2. Consequently, they are very active in the vaginal assay. Since they are cleaved by esterase(s) at a relatively low rate, RHAs of about 2%, our model would predict them to have a relatively high systemic (uterotrophic) action. However, neither of these 15α-alkyl esters produce a statistically significant estrogenic response in the uterus at the 100 μg dose. As described above, the systemic effect of the 15α-analogs is lower than that produced by E16-1,2$F_1$ which we previously found shows the greatest differential action. Thus, the uterotrophic activity of E15-1,1 and E15-1,2 was unusually low for all of these $E_2$-alkyl esters.

The fact that E15-1,1 and E15-1,2 show such divergence between the Ishikawa assay (where they are almost as potent as $E_2$) and the uterotrophic assay (where they are either inactive or almost inactive) demonstrates their unusual susceptibility to catabolism, likely through esterase hydrolysis. This discrepancy between the uterotropic and Ishikawa assays is strong evidence that these esters of the $E_2$-carboxylates are acting as labile estrogens, since generally the potency of estrogens in the Ishikawa assay closely mirrors in vivo activity.[38] The low systemic activity of E15-1,1 and E15-1,2, in spite of their low enzymatic hydrolysis, appear to contradict the "soft" estrogen model. How can estrogens that are enzymatically hydrolyzed at low rates (E15-1,1 and E15-1,2) seem to have the qualities of local estrogens? The RBA and RSA of the carboxylate, E15-1,0, is very low, not measurable, but as discussed above the hydrolysis of the 15-esters by esterase is relatively slow. However, this rate of hydrolysis is evidently sufficient to hydrolytically deactivate these E15-1 esters. Additionally, the rate of esterase hydrolysis of the $E_2$-analogs measures only one of the potential catabolic routes of metabolism, albeit the one designed to play the major role. It is well known that the major secretory estrogen, $E_2$, is metabolized by a large number of catabolic enzymes. While in the case of the $E_2$-analogs the esterase enzyme probably plays the most important role, there are other enzymatic routes that also inactivate these steroids. Substituents on $E_2$-analogs are known to affect these enzymes and play an important role in their metabolic clearance. For example, substituents at C-11 protect steroidal estrogens from metabolism, specifically from the metabolically important 2-hydroxylase 44 and thus, such substituents at C-11 have a major impact, decreasing metabolic clearance and increasing potency.[45] Conversely, substitution at 15α- could increase metabolism and therefore decrease the biological $t_{1/2}$ of the E15-1 analogs. Thus, increased metabolism in concert with enzymatic hydrolysis would eliminate systemic activity.

Nevertheless, regardless of the reason, the 15α-alkyl esters, E15-1,1 and E15-1,2 have the characteristics of a "soft" estrogen. Interestingly, E15-1,1 and E15-1,2, is as potent in stimulating a vaginal response as E16-1,2$F_1$, the best compound in our previous study.[20] However, as discussed above, E15-1,1 and E15-1,2 were inactive in the uterotrophic assay, in contrast to E16-1,2$F_1$, which produced a small but statistically significant response. Thus, the E15-esters have an improved local to systemic estrogenic profile. E15-1,1 and E15-1,2 have excellent potential for being useful "soft" therapeutic agents for the local treatment of estrogen deprivation.

REFERENCES

1) Shlipak, M. G.; Simon, J. A.; Vittinghoff, E.; Lin, F.; Barrett-Connor, E.; Knopp, R. H.; Levy, R. I.; Hulley, S. B. Estrogen and Progestin, Lipoprotein(a), and the Risk of Recurrent Coronary Heart Disease Events After Menopause. *JAMA*. 2000, 283, 1845–1852.
2) Beral, V.; Banks, E.; Reeves, G.; Appleby, P. Use of HRT and the Subsequent Risk of Cancer. *J Epidemiol Biostat*. 1999, 4, 191–210.
3) Banks, E.; Beral, V. Hormone Replacement Therapy for Secondary Prevention of Coronary Heart Disease. *JAMA*. 1999, 281, 794–797.
4) Beral, V.; Hermon, C.; Kay, C.; Hannaford, P.; Darby, S.; Reeves, G. Mortality Associated With Oral Contraceptive Use: 25 Year Follow Up of Cohort of 46 000 Women From Royal College of General Practitioners' Oral Contraception Study. *BMJ*. 1999, 318, 96–100.
5) Sarrel, P. M. Sexuality and Menopause. *Obstetrics and Gynecology*. 1990, 75, 26S–30S.
6) Sarrel, P. M. Sexuality. In *The Menopause*; Studd, J., Whithead, M. I., Eds.; Blackwell Scientific Publications: London, England, 1988; pp 65–75.
7) Hasselquist, M. B.; Goldberg, N.; Schroeter, A.; Spelsberg, T. C. Isolation and Characterization of the Estrogen Receptor in Human Skin. *J. Clin. Endocrinol. Metab.* 1980, 50, 76–82.
8) Punnonen, R.; Lovgren, T.; Kouvonen, I. Demonstration of Estrogen Receptors in the Skin. *J. Endocrinol. Invest.* 1980, 3, 217–221.
9) Uzuka, M.; Nakajima, K.; Ohta, S.; Mori, Y. The Mechanism of Estrogen-Induced Increase in Hyaluronic Acid Biosynthesis, With Special Reference to Estrogen Receptor in the Mouse Skin. *Biochim. Biophys. Acta*. 1980, 627, 199–206.
10) Schiff, I.; Tulchinsky, D.; Ryan, K. J. Vaginal Absorption of Estrone and 17b-Estradiol. *Fertility and Sterility*. 1977, 28, 1063–1066.
11) Rigg, L. A.; Hermann, H.; Yen, S. S C. Absorption of Estrogens From Vaginal Creams. *N. Engl. J. Med.* 1978, 298, 195–197.
12) Martin, P. L.; Yen, S. S C.; Burnier, A. M.; Hermann, H. Systemic Absorption and Sustained Effects of Vaginal Estrogen Creams. *JAMA*. 1979, 242, 2699–2700.
13) Schiff, I.; Tulchinsky, D.; Ryan, K. J.; Kadner, S.; Levitz, M. Plasma Estriol and Its Conjugates Following Oral and Vaginal Administration of Estriol to Postmenopausal Women: Correlations With Gonadotropin Levels. *Am. J. Obstet. Gynecol.* 1980, 138, 1137–1141.
14) Bodor, N. Designing Safer Drugs Based on the Soft Drug Approach. *Trends Pharmac Sci.* 1982, 3, 53–56.
15) Graffner-Nordberg, M.; Sjodin, K.; Tunek, A.; Hallberg, A. Synthesis and Enzymatic Hydrolysis of Esters, Constituting Simple Models of Soft Drugs. *Chem Pharm Bull (Tokyo)*. 1998, 46, 591–601.
16) Laurent, H.; Gerhards, E.; Wiechert, R. New Biologically Active Pregnan-21-Oic Acid Esters. *J Steroid Biochem.* 1975, 6, 185–192.
17) Druzgala, P.; Hochhaus, G.; Bodor, N. Soft Drugs—10. Blanching Activity and Receptor Binding Affinity of a New Type of Glucocorticoid: Loteprednol Etabonate. *J Steroid Biochem Mol Biol.* 1991, 38, 149–154.
18) Lee, H. J.; Soliman, M. R. I. Anti-Inflammatory Steroids Without Pituitary Adrenal Suppression. *Science*. 1982, 215, 989–991.
19) Bucourt, R.; Vignau, M.; Torelli, V. New Biospecific Adsorbents for the Purification of Estradiol Receptor. *J. Biol. Chem.* 1978, 253, 8221–8228.
20) Labaree, D. C.; Reynolds, T. Y.; Hochberg, R. B. Estradiol-16α-Carboxylic Acid Esters As Locally Active Estrogens. *J Med Chem.* 2001, 44, 1802–1814.
21) Anstead, G. M.; Carlson, K. E.; Katzenellenbogen, J. A. The Estradiol Pharmacophore: Ligand Structure-Estrogen Receptor Binding Affinity Relationships and a Model for the Receptor Binding Site. *Steroids.* 1997, 62, 268–303.

22) Cantrall, E. W.; Littell, R.; Bernstein, S. The Synthesis of C-15-Substituted Estra-1,3,5(10)-Trienes. I; *J. Org. Chem.* 1964, 29, 64–68.

23) Cantrall, E. W.; Littell, R.; Bernstein, S. The Synthesis of C-15 β-Substituted Estra-1,3,5(10)-Trienes. II. *J. Org. Chem.* 1964, 29, 214–217.

24) Nambara, T.; Sudo, K.; Sudo, M. Syntheses of Estetrol Monoglucuronides. *Steroids.* 1976, 27, 111–122.

25) Groen, M. B.; Zeelen, F. J. Biomimetic Total Synthesis of Steoids. 4. Stereoselective Synthesis of 15alpha-Methyl-19-Norsteroids. *Recueil des Travaux Chimiques des Pays-Bas-Journal of the Royal Netherlands Chemical Society.* 1979, 98, 239–242.

26) Noyce, D. S.; Denney, D. B. Steric Effects and Stereochemistry of Lithium Aluminum Hydride Reduction. *J Am Chem Soc.* 1950, 72, 5743–5745.

27) Vaughan, W. R.; Perry jr, R. The Configuration of Isocamphenilanol. *J Am Chem Soc.* 1952, 74, 5355–5356.

28) Bojack, G.; Kinzer, H. An Oxy-Cope Rearrangement Approach to C(15)α-Alkylated Derivatives of Estradiol. *Tetrahedron Letters.* 1994, 35, 9025–9026.

29) Miyake, Y.; Kubo, Y.; Iwabuchi, S.; Kojima, M. Syntheses of 15 Alpha- and 15 Beta-Carboxymethyltestosterone Bovine Serum Albumin Conjugates: Characteristics of the Antisera to Testosterone. *Steroids.* 1982, 40, 245–259.

30) Dionne, P.; Ngatcha, B. T.; Poirier, D. D-Ring Allyl Derivatives of 17 Beta- and 17 Alpha-Estradiols: Chemical Synthesis and $^{13}$C NMR Data. *Steroids.* 1997, 62, 674–681.

31) Still, C. W.; Kahn, M.; Mitra, A. Rapid Chromatographic Technique for Preparative Separations With Moderate Resolution. *J. Org. Chem.* 1978, 43, 2923–2925.

32) Fried J and Edwards J A Eds. *Organic Reactions in Steriod Chemistry*; Van Nostrand Reinhold Co.: New York, 1972; pp 314

33) Kuiper, G. G.; Carlsson, B.; Grandien, K.; Enmark, E.; Haggblad, J.; Nilsson, S.; Gustafsson, J. A. Comparison of the Ligand Binding Specificity and Transcript Tissue Distribution of Estrogen Receptors Alpha and Beta. *Endocrinology.* 1997, 138, 863–870.

34) Hochberg, R. B.; Rosner, W. The Interaction of 16α-[$^{125}$I]Iodoestradiol With Estrogen Receptor and Other Binding Proteins. *Proc. Natl. Acad. Sci. USA.* 1980, 77, 328–332.

35) Green, S.; Walter, P.; Kumar, V.; Krust, A.; Bomert, J. M.; Argos, P.; Chambon, P. Human Oestrogen Receptor CDNA: Sequence, Expression and Homology to V-Erb-A. *Nature.* 1986, 320, 134–139.

36) Ogawa, S.; Inoue, S.; Watanabe, T.; Hiroi, H.; Orimo, A.; Hosoi, T.; Ouchi, Y.; Muramatsu, M. The Complete Primary Structure of Human Estrogen Receptor Beta (HER Beta) and Its Heterodimerization With ER Alpha in Vivo and in Vitro. *Biochem Biophys Res Commun.* 1998, 243, 122–126.

37) Harris, H. A.; Bapat, A. R.; Gonder, D. S.; Frail, D. E. The Ligand Binding Profiles of Estrogen Receptors Alpha and Beta Are Species Dependent. *Steroids.* 2002, 67, 379–384.

38) Littlefield, B. A.; Gurpide, E.; Markiewicz, L.; McKinley, B.; Hochberg, R. B. A Simple and Sensitive Microtiter Plate Estrogen Bioassay Based on Stimulation of Alkaline Phosphatase in Ishikawa Cells: Estrogenic Action of D$^5$ Adrenal Steroids. *Endocrinology.* 1990, 127, 2757–2762.

39) Emmens, C. W. Estrogens. In *Methods in Hormone Research*; Dorfman, R. I., Ed.; Academic Press Inc.: New York, 1962; pp 59–111.

40) Martin, L. The Use of 2-3-5-Triphenyltetrazolium Chloride in the Biological Assay of Oestrogens. *J. Endocrin.* 1960, 20, 187–197.

41) Schottler, C.; Krisch, K. Hydrolysis of Steroid Hormone Esters by an Unspecific Carboxylesterase From Pig Liver Microsomes. *Biochem. Pharmacol.* 1974, 23, 2867–2875.

42) Kuiper, G. G.; Lemmen, J. G.; Carlsson, B.; Corton, J. C.; Safe, S. H.; van der Saag, P. T.; Van der Burg, B.; Gustafsson, J. A. Interaction of Estrogenic Chemicals and Phytoestrogens With Estrogen Receptor Beta. *Endocrinology.* 1998, 139, 4252–4263.

43) Shughrue, P. J.; Lane, M. V.; Merchenthaler, I. Biologically Active Estrogen Receptor-Beta: Evidence From in Vivo Autoradiographic Studies With Estrogen Receptor Alpha-Knockout Mice. *Endocrinology.* 1999, 140, 2613–2620.

44) Salmon, J.; Coussediere, D.; Cousty, C.; Raynaud, J. P. Pharmacokinetics and Metabolism of Moxestrol in Humans. *J Steroid Biochem.* 1983, 18, 565–573.

45) Zielinski, J. E.; Yabuki, H.; Pahuja, S. L.; Lamer, J. M.; Hochberg, R. B. 16α-[$^{125}$I]Iodo-11b-Methoxy-17β-Estradiol: A Radiochemical Probe for Estrogen Sensitive Tissues. *Endocrinology.* 1986, 119, 130–139.

The invention claimed is:

1. A compound according to the structure:

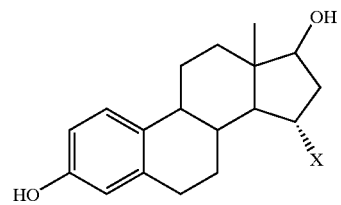

where X is

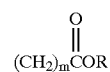

R is H, a $C_1$ to $C_5$ alkyl group optionally substituted with at least one halogen group; and m is from 0–5, and pharmaceutically acceptable salts, solvates or polymorphs thereof.

2. The compound according to claim 1 wherein R is a $C_1$ to $C_5$ alkyl group optionally substituted with at least one halogen group and m is from 0–2.

3. The compound according to claim 1 wherein R is methyl, ethyl, propyl, iso-propyl, butyl, iso-butyl, pentyl, neo-pentyl or $CH_2CH_2F$; and m is 0.

4. The compound according to claim 3 wherein m is 0 and R is methyl, ethyl or $CH_2CH_2F$.

5. The compound according to claim 4 wherein R is methyl.

6. The compound according to claim 4 wherein R is ethyl.

7. The compound according to claim 4 wherein R is $CH_2CH_2F$.

8. The compound according to claim 1 wherein R is $CH_2CHF_2$.

9. The compound according to claim 1 wherein R is $CH_2CF_3$.

10. A compound according to claim 1, wherein R is a $C_1$ to $C_5$ alkyl, which may be unsubstituted or substituted with at least one F group.

11. The compound according to claim 1 wherein R is methyl, ethyl or $CH_2CH_2F$.

12. A compound according to the structure:

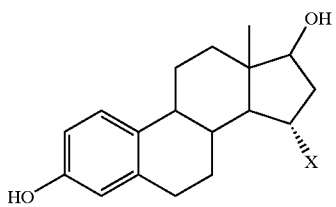

where X is

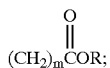

R is H; and m is from 0, 2, 3, 4, or 5, and pharmaceutically acceptable salts, solvates polymorphs thereof.

13. The compound according to claim 12 wherein m is 0.

14. The compound according to claim 12 wherein m is 2, 3, 4, or 5.

15. A pharmaceutical composition consisting essentially of an effective amount of a compound for alleviating the symptomology of menopause in a patient, said compound having the structure:

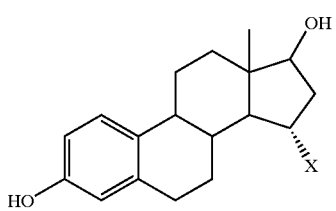

where X is

R is a $C_1$ to $C_5$ alkyl group, optionally substituted with at least one halogen group; and m is from 0–5, and pharmaceutically acceptable salts, solvates or polymorphs, optionally in combination with a pharmaceutically acceptable carrier, excipient or additive.

16. The composition according to claim 15 wherein R is a $C_1$ to $C_5$ alkyl group optionally substituted with at least fluorine group, and m is from 0–2.

17. The composition according to claim 15 wherein R is methyl, ethyl, propyl, iso-propyl, butyl, iso-butyl, pentyl, neo-pentyl, $CH_2CH_2F$ or $CH_2CF_3$ and m is 0.

18. The composition according to claim 17 wherein m is 0 and R is methyl, ethyl or $CH_2CH_2F$.

19. The composition according to claim 17 wherein R is methyl.

20. The composition according to claim 17 wherein R is ethyl.

21. The composition according to claim 17 wherein R is $CH_2CH_2F$.

22. The composition according to claim 15 in topical dosage form.

23. The composition according to claim 15 formulated as a vaginal cream, gel, lotion or suppository.

24. A pharmaceutical composition consisting essentially of an effective amount of a compound for alleviating the symptomology of menopause in a patient, said compound having the structure:

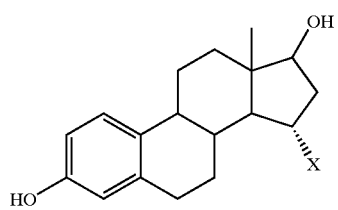

where X is

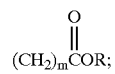

R is H; and m is from 0, 2, 3, 4, or 5, and pharmaceutically acceptable salts, solvates or polymorphs thereof, optionally in combination with a pharmaceutically acceptable carrier, excipient or additive.

25. The composition according to claim 24 wherein m is 0.

26. The composition according to claim 24 wherein m is 2, 3, 4, or 5.

27. A method for alleviating the symptoms of menopause, comprising administering to a patient in need of therapy a pharmaceutical composition comprising an effective amount of a compound according to the structure:

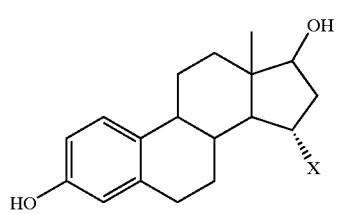

where X is

R is H or a $C_1$ to $C_5$ alkyl group, optionally substituted with at least one halogen group;

and m is from 0–5, and pharmaceutically acceptable salts, solvates or polymorphs thereof, optionally in combination with a pharmaceutically acceptable carrier, excipient or additive.

28. The method according to claim 27 wherein R is a $C_1$ to $C_5$ alkyl group or a $CH_2CH_2F$ group; and m is from 0–2.

29. The method according to claim 27 wherein said symptom of menopause is selected from the group consisting of bone loss associated with osteoporosis and vaginal dyspareunia.

30. The method according to claim 27 wherein said symptom of menopause is vaginal dyspareunia and said composition is administered to the patient's vaginal membranes.

31. The method according to claim 28 wherein R is methyl.

32. The method according to claim 28 wherein R is ethyl.

33. The method according to claim 28 wherein R is $CH_2CH_2F$.

34. The method according to claim 28 wherein R is $CH_2CHF_2$.

35. The method according to claim 28 wherein R is $CH_2CF_3$.

36. The method according to claim 30 wherein said composition is administered as a vaginal cream, gel, lotion or suppository.

37. The method according to claim 27 wherein said composition is administered within the patient's body from an implant.

38. The method according to claim 27 wherein said symptom of menopause is bone loss associated with osteoporosis and said composition is administered within the patient's body from an implant.

* * * * *